United States Patent
Cassella et al.

(10) Patent No.: US 12,285,432 B2
(45) Date of Patent: Apr. 29, 2025

(54) TREATMENT OF HAIR LOSS DISORDERS WITH DEUTERATED JAK INHIBITORS

(71) Applicant: Sun Pharmaceutical Industries, Inc., Princeton, NJ (US)

(72) Inventors: James V. Cassella, Essex, CT (US); Christopher L. Brummel, Marlborough, MA (US)

(73) Assignee: Sun Pharmaceutical Industries, Inc., Princeton, NJ (US)

( * ) Notice: Subject to any disclaimer, the term of this patent is extended or adjusted under 35 U.S.C. 154(b) by 0 days.

(21) Appl. No.: 18/382,307

(22) Filed: Oct. 20, 2023

(65) Prior Publication Data

US 2024/0058345 A1    Feb. 22, 2024

Related U.S. Application Data

(63) Continuation of application No. PCT/US2022/040115, filed on Aug. 11, 2022.

(60) Provisional application No. 63/232,107, filed on Aug. 11, 2021.

(51) Int. Cl.
*A61K 31/519* (2006.01)
*A61K 45/06* (2006.01)

(52) U.S. Cl.
CPC ............ *A61K 31/519* (2013.01); *A61K 45/06* (2013.01)

(58) Field of Classification Search
CPC ........ A61K 31/519; A61K 45/06; A61P 17/14
See application file for complete search history.

(56) References Cited

U.S. PATENT DOCUMENTS

| | | |
|---|---|---|
| 7,598,257 B2 | 10/2009 | Rodgers et al. |
| 9,198,911 B2 | 12/2015 | Christiano et al. |
| 9,249,149 B2 | 2/2016 | Silverman et al. |
| 9,662,335 B2 | 5/2017 | Rodgers et al. |
| 10,265,258 B2 | 4/2019 | Christiano et al. |
| 10,561,659 B2 | 2/2020 | Wagner et al. |
| 11,298,570 B2 | 4/2022 | Christiano et al. |
| 2007/0135461 A1 | 6/2007 | Rodgers et al. |
| 2008/0312258 A1 | 12/2008 | Rodgers et al. |
| 2014/0135350 A1 | 5/2014 | Ni et al. |
| 2015/0197525 A1 | 7/2015 | Silverman et al. |
| 2015/0239896 A1 | 8/2015 | Silverman et al. |

FOREIGN PATENT DOCUMENTS

| | | | |
|---|---|---|---|
| WO | WO-2007065167 A1 * | 6/2007 | ............ A61K 31/66 |
| WO | WO-2012/061537 A2 | 5/2012 | |
| WO | WO-2013/149194 A1 | 10/2013 | |
| WO | WO-2014/078486 A1 | 5/2014 | |
| WO | WO-2015/120110 A2 | 8/2015 | |
| WO | WO-2017/192905 A1 | 11/2017 | |
| WO | WO-2023/018904 | 2/2023 | |

OTHER PUBLICATIONS

Anonymous, "Guidance for Industry Drug Interaction Studies-Study Design, Data Analysis, Implications for Dosing, and Labeling Recommendations, Draft Guidance", Clinical Pharmacology, pp. 2-75, XP055667243 (2012).
Baille, "The Use of Stable Isotopes in Pharmacological Research," *Pharmacological Reviews*, 33(2): 81-132 (1981).
Buteau, "Deuterated Drugs: Unexpectedly Nonobvious?," *Journal of High Technology Law, Suffolk University Law School*, XI: 22-74 (2009).
Cassella et al., CTP-543, an Oral JAK Inhibitor, *Achieves Primary Endpoint in Phase 2 Randomized, Placebo-Controlled Dose-Ranging Trial in Patients with Moderate-to-Severe Alopecia Areata*, European Academy of Dermatology and Venereology Annual Congress (Oct. 12, 2019).
Craiglow et al., "Killing Two Birds with One Stone: Oral Tofacitinib Reverses Alopecia Universalis in a Patient with Plaque Psoriasis," J Investig Dermatol 134:2988-2990 (2014).
Craiglow et al., "Topical Ruxolitinib for the Treatment of Alopecia Universalis," JAMA Dermatol 152(4):490-491 (2016).
CTP-543 Phase 2 Results in Patients with Moderate-to-Severe Alopecia Areata. Concert Pharmaceuticals Inc. Presentation on Sep. 3, 2019.
Delamere et al., "Interventions for alopecia areata (Review)," Cochrane Database of Sys Revs 2 (2008).
Fisher et al., "The Complexities Inherent in Attempts to Decrease Drug Clearance by Blocking Sites of CYP-Mediated Metabolism," Curr Opin Drug Discov Devel, 9(1): 101-109 (2006).
Foster, "Deuterium Isotope Effects in Studies of Drug Metabolism," *Trends in Pharmacological Sciences*, 5: 524-527 (1984).
Foster, "Deuterium Isotope Effects in the Metabolism of Drugs and Xenobiotics: Implications for Drug Design," *Advances in Drug Research*, 14: 1-40 (1985).
Fukuto et al., "Determination of the Mechanism of Demethylenation of (Methylenedioxy)phenyl Compounds by Cytochrome P450 Using Deuterium Isotope Effects," J. Med. Chem. 34: 2871-2876, 1991.

(Continued)

*Primary Examiner* — Savitha M Rao
*Assistant Examiner* — Andrew P Lee
(74) *Attorney, Agent, or Firm* — MEDLER FERRO WOODHOUSE & MILLS PLLC

(57) ABSTRACT

A method of treating a JAK-inhibition-responsive condition (such as a hair loss disorder) in a human subject in need thereof, the method comprising administering to the human subject a therapeutically effective amount of Compound (I) or a pharmaceutically acceptable salt thereof, wherein each position designated specifically as deuterium has at least 95% incorporation of deuterium; and wherein: the subject is receiving a concomitant administration of a CYP3A4 inhibitor; and the therapeutically effective amount of Compound (I), or a pharmaceutically acceptable salt thereof, is not reduced compared to the therapeutically effective amount of Compound (I), or pharmaceutically acceptable salt thereof, that would be administered to the subject in the absence of concomitant administration of a CYP3A4 inhibitor.

28 Claims, No Drawings

(56) References Cited

OTHER PUBLICATIONS

Harris et al., "Rapid skin repigmentation on oral ruxolitinib in a patient with coexistent vitiligo and alopecia areata," J Amer Acad Dermatol 74(2):370-371 (Feb. 2016).
International Search Report and Written Opinion for International Application No. PCT/US2022/040115, dated Nov. 18, 2022.
Jakafi® (ruxolitinib) Prescribing Information, Revised Jan. 2020 pp. 1-40.
King Brett et al: "Phase 2 randomized, dose-ranging trial of CTP-543, a selective Janus Kinase inhibitor, in moderate-to-severe alopecia areata", Journal of the American Academy of Dermatology, Mosby, Inc, US, vol. 87, No. 2, Mar. 29, 2022 (Mar. 29, 2022), pp. 306-313, XP087119899, ISSN: 0190-9622, DOI: 10.1016/J.JAAD. 2022.03.045 [retrieved on Mar. 29, 2022].
Mackay-Wiggan et al., "Oral ruxolitinib induces hair regrowth in patients with moderate-to-severe alopecia areata," J. Clin. Invest. Insight (Sep. 22, 2016).
Ostojic et al., "Ruxolitinib: a new JAK1/2 Inhibitor that Offers Promising Options for Treatment of Myelofibrosis," *Future Oncology*, 7(9):1035-1043 (2011).
Pieri et al., "Ruxolitinib-induced reversal of alopecia universalis in a patient with essential thrombocythemia," AJH 90(1):82-83 (2015).
Press Release "Concert Pharmaceuticals Announces CTP-543 Positive Top-Line Phase 1 Results," Dec. 14, 2016.
Press Release "Concert Pharmaceuticals Reports Positive CTP-543 Results from Phase 2 Alopecia Areata Trial," Sep. 3, 2019 [Date Accessed: Oct. 17, 2019].
Shi et al., "The Effect of CYP3A4 Inhibition or Induction on the Pharmacokinetics and Pharmacodynamics of Orally Administered Ruxolitinib (INCB018424 Phosphate) in Healthy Volunteers," J Clin Pharmacol 52:809-818 (2012).
Shi et al., "The pharmacokinetics, pharmacodynamics and safety of orally dosed INC18424 phosphate in healthy volunteers," J. Clin. Pharmacol, 51:1644-1654 (2011).
Shilling et al., "Metabolism, Excretion, and Pharmacokinetics of [14C]INCB018424, A Selective Janus Tyrosine Kinase 1/2 Inhibitor, in Humans," *Drug Metabolism and Disposition*, 38(11):2023-2031 (2010).
Silvestri et al., *Ruxolitinib for the treatment of alopecia areata*, Ital. J. Med. 10(Suppl. 2):108 (2016).
Vandiver et al., "Two cases of alopecia areata treated with ruxolitinib: a discussion of ideal dosing and laboratory monitoring," Int J Dermatol 56:833-835 (2017).
Wolen, "The Application of Stable Isotopes to Studies of Drug Bioavailability and Bioequivalence," J Clin Pharmacol, 26: 419-424 (1986).
Xing et al., "Alopecia areata is driven by cytotoxic T lymphocytes and is reversed by JAK inhibition," Nature Med. 20: 1043-49 (2014).
Grounds of Appeal in European Opposition; European Patent Application No. 18188152.5, Jun. 26, 2024.
Petition for Inter Partes Review of Claims 1-15 of U.S. Pat. No. 9,249,149; Inter Partes Review 2017-01256 (U.S. Pat. No. 9,249,149), Apr. 7, 2017.
Declaration of F. Peter Guengrich; Inter Partes Review 2017-01256 (U.S. Pat. No. 9,249,149), Apr. 7, 2017.
Patent Owner Preliminary Response; Inter Partes Review 2017-01256 (U.S. Pat. No. 9,249,149), Jul. 24, 2017.
Petitioner's Request for Rehearing of U.S. Pat. No. 9,249,149; Inter Partes Review 2017-01256 (U.S. Pat. No. 9,249,149), Nov. 13, 2017.
Decision Denying Institution of Inter Partes Review; Inter Partes Review 2017-01256 (U.S. Pat. No. 9,249,149), Oct. 19, 2017.
Decision Granting Petitioner's Request for Rehearing; Inter Partes Review 2017-01256 (U.S. Pat. No. 9,249,149), Apr. 9, 2018.
Decision Institution of Inter Partes Review; Inter Partes Review 2017-01256 (U.S. Pat. No. 9,249,149), Apr. 9, 2018.
Inter Partes Review Certificate; Inter Partes Review 2017-01256 (U.S. Pat. No. 9,249,149) issued Apr. 2, 2024.
Petition for Post-Grant Review, Post Grant Review PGR2017-00034 (U.S. Pat. No. 9,662,335), Jun. 27, 2018.
Decision Denying Institution of Post-Grant Review; Post Grant Review PGR2017-00034 (U.S. Pat. No. 9,662,335), Jan. 11, 2018.
Federal Circuit Decision in *Sun Pharmaceutical Industries, Inc., F/D/B/A Concert Pharmaceuticals, Inc.. v. Incyte Corporation*, United States Court of Appeals for the Federal Circuit, Case No. 19-2011, Aug. 22, 2023.

* cited by examiner

TREATMENT OF HAIR LOSS DISORDERS WITH DEUTERATED JAK INHIBITORS

RELATED APPLICATION(S)

This application is a continuation of International Application No. PCT/US22/40115, which designated the United States and was filed on Aug. 11, 2022, published in English, which claims the benefit of U.S. Provisional Application 63/232,107, filed on Aug. 11, 2021. The entire teachings of the above application are incorporated herein by reference.

BACKGROUND OF THE INVENTION

Patients often take multiple medications at once, which can give rise to drug-drug interactions. Drug-drug interactions occur when two or more drugs both interact with the same metabolic enzymes, altering the total exposure to the administered drugs and creating additional or more severe side effects. Drug-drug interactions can also occur when one drug inhibits the enzyme that metabolizes the second drug, thereby increasing the concentration of the second drug in the blood stream, leading to an increased risk of side effects. Depending on the severity of the interactions, patients may need to modify the dose of one or both medications, or may even need to discontinue use of one of the medications.

According to the FDA, unanticipated or unrecognized drug-drug interactions are an important cause of morbidity and mortality associated with prescription drugs. The FDA has set forth guidelines on conducting drug-drug interaction studies, to aid in drug labeling and limit adverse events caused by drug-drug interactions. For drugs that are metabolized by CYP 450 enzymes, the FDA provides a list of inhibitors by enzyme for conducting clinical studies on drug-drug interactions. Ketoconazole and itraconazole are among the strong CYP3A4 inhibitors to use for testing drug-drug interactions.

Ruxolitinib phosphate, is a heteroaryl-substituted pyrrolo[2,3-d]pyrimidines also known as 3(R)-cyclopentyl-3-[4-(7H-pyrrolo[2,3-d]pyrimidin-4-yl)-1H-pyrazol-1-yl]propanenitrile phosphate and as (R)-3-(4-(7H-pyrrolo[2,3-d]pyrimidin-4-yl)-1H-pyrazol-1-yl)-3-cyclopentylpropanenitrile phosphate, inhibits Janus Associated Kinases (JAKs) JAK1 and JAK2. These kinases mediate the signaling of a number of cytokines and growth factors important for hematopoiesis and immune function. JAK signaling involves recruitment of STATs (signal transducers and activators of transcription) to cytokine receptors, activation and subsequent localization of STATs to the nucleus leading to modulation of gene expression.

Ruxolitinib phosphate is currently approved for the treatment of patients with intermediate or high-risk myelofibrosis, including primary myelofibrosis, post-polycythemia vera myelofibrosis and post-essential thrombocythemia myelofibrosis. Ruxolitinib phosphate is also currently in clinical trials for the treatment of additional conditions.

Ruxolitinib has known drug-drug interactions with strong CYP3A4 inhibitors. These interactions are severe enough that the prescribing information for ruxolitinib requires dose modifications for concomitant dosing with strong CYP3A4 inhibitors, including boceprevir, clarithromycin, conivaptan, indinavir, itraconazole, ketoconazole, lopinavir/ritonavir, mibefradil, nefazodone, nelfinavir, posaconazole, ritonavir, saquinavir, telaprevir, telithromycin and voriconazole.

The ruxolitinib prescribing information describes a drug-drug interactions study in healthy volunteers, where the subjects were administered ruxolinitib before and after taking ketoconazole. The study administered a single dose of 10 mg of ruxolitinib on Day 1, 200 mg twice a day of ketoconazole on Days 2-4, and 10 mg of ruxolitinib plus 200 mg of ketoconazole on Day 5. The $C_{max}$ of ruxolitinib increased by 33%, the AUC increased by 91%, and the half-life increased from 3.7 hour to 6.0 hours as a result of dosing ruxolitinib with ketoconazole. These changes are significant, and warrant the caution in the label about concomitant administration of ruxolitinib with strong CYP3A4 inhibitors.

Despite the beneficial activities of ruxolitinib, there is a continuing need for new compounds that inhibit JAK1 and JAK2, but which are not adversely impacted by concomitant administration of a CYP3A4 inhibitor.

SUMMARY OF THE INVENTION

It has now been found that Compound (I), also referred to as (R)-3-(4-(7H-pyrrolo[2,3-d]pyrimidin-4-yl)-1H-pyrazol-1-yl)-3-(cyclopentyl-2,2,3,3,4,4,5,5-$d_8$)propanenitrile, or D8-ruxolitinib), which is useful for the treatment of JAK-inhibition-responsive conditions, including hair-loss disorders such as alopecia areata, unexpectedly does not require a dose adjustment or interruption in treatment when co-administered with a strong CYP3A4 inhibitor.

In a first embodiment, the invention relates to a method of treating a JAK-inhibition-responsive condition (such as a hair loss disorder) in a human subject in need thereof, the method comprising administering to the human subject a therapeutically effective amount of Compound (I) represented by the following structural formula:

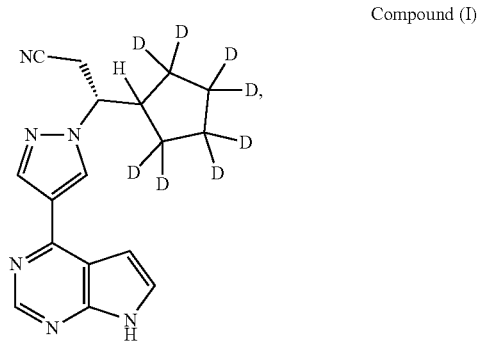

Compound (I)

or a pharmaceutically acceptable salt thereof, wherein each position designated specifically as deuterium has at least 95% incorporation of deuterium; and wherein:
(i) the subject is receiving a concomitant administration of a CYP3A4 inhibitor; and
(ii) the therapeutically effective amount of Compound (I), or a pharmaceutically acceptable salt thereof, is not reduced compared to the therapeutically effective amount of Compound (I), or pharmaceutically acceptable salt thereof, that would be administered to the subject in the absence of concomitant administration of a CYP3A4 inhibitor.

In a second embodiment, the invention relates to a method of treating a JAK-inhibition-responsive condition (such as a hair loss disorder) in a human subject in need thereof, the method comprising administering to the human subject a therapeutically effective amount of Compound (I) represented by the following structural formula:

Compound (I)

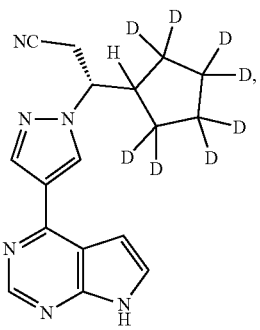

or a pharmaceutically acceptable salt thereof, wherein each position designated specifically as deuterium has at least 95% incorporation of deuterium; and
wherein:
(i) the subject has been determined to be receiving a concomitant administration of a CYP3A4 inhibitor; and
(ii) the therapeutically effective amount of Compound (I), or a pharmaceutically acceptable salt thereof, is not reduced compared to the therapeutically effective amount of Compound (I), or pharmaceutically acceptable salt thereof, that would be administered to the subject in the absence of concomitant administration of a CYP3A4 inhibitor.

In a third embodiment, the invention relates to a method of treating a JAK-inhibition-responsive condition (such as a hair loss disorder) in a human subject in need thereof, the method comprising the steps of: receiving information related to whether the patient is receiving a concomitant administration of a CYP3A4 inhibitor; and administering to the human subject a therapeutically effective amount of Compound (I) represented by the following structural formula:

Compound (I)

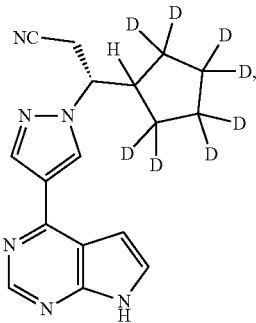

or a pharmaceutically acceptable salt thereof, wherein each position designated specifically as deuterium has at least 95% incorporation of deuterium; and
wherein:
(i) the information indicates that the subject is receiving concomitant administration of a CYP3A4 inhibitor; and
(ii) the therapeutically effective amount of Compound (I), or a pharmaceutically acceptable salt thereof, is not reduced compared to the therapeutically effective amount of Compound (I), or pharmaceutically acceptable salt thereof, that would be administered to the subject in the absence of concomitant administration of a CYP3A4 inhibitor.

In a fourth embodiment, the invention relates to a method of treating a JAK-inhibition-responsive condition (such as a hair loss disorder) in a human subject in need thereof, the method comprising the steps of:
selecting the human subject on the basis that the human subject is receiving a concomitant administration of a CYP3A4 inhibitor; and
administering to the selected human subject a therapeutically effective amount of Compound (I) represented by the following structural formula:

Compound (I)

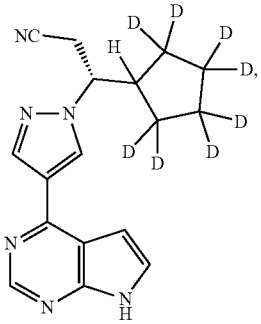

or a pharmaceutically acceptable salt thereof, wherein each position designated specifically as deuterium has at least 95% incorporation of deuterium; and wherein, the therapeutically effective amount of Compound (I), or a pharmaceutically acceptable salt thereof, is not reduced compared to the therapeutically effective amount of Compound (I), or pharmaceutically acceptable salt thereof, that would be administered to the subject in the absence of concomitant administration of a CYP3A4 inhibitor.

In a fifth embodiment, the invention relates to a method of treating a JAK-inhibition-responsive condition (such as a hair loss disorder) in a human subject in need thereof, the method comprising the steps of:
obtaining a blood sample from the subject
determining a pre-dose level (i.e., before administration of Compound (I)) of a
CYP3A4 inhibitor in the blood sample; and
administering a therapeutically effective amount of a compound to the subject, wherein the pre-dose level of the CYP3A4 inhibitor in the blood sample indicates that the subject is receiving concomitant administration of a CYP3A4 inhibitor, wherein the compound is Compound (I) represented by the following structural formula:

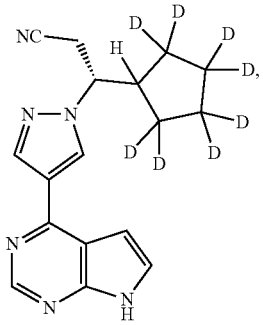

Compound (I)

or a pharmaceutically acceptable salt thereof, wherein each position designated specifically as deuterium has at least 95% incorporation of deuterium; and
wherein, the therapeutically effective amount of Compound (I), or a pharmaceutically acceptable salt thereof, is not reduced compared to the therapeutically effective amount of Compound (I), or pharmaceutically acceptable salt thereof, that would be administered to the subject in the absence of concomitant administration of a CYP3A4 inhibitor.

In a sixth embodiment, the invention relates to a method of treating a JAK-inhibition-responsive condition (such as a hair loss disorder) in a human subject in need thereof, the method comprising:
(i) determining if the human subject is receiving a concomitant administration of a CYP3A4 inhibitor; and
(ii) administering to the human subject a therapeutically effective amount of Compound (I) if the subject is receiving concomitant administration of a CYP3A4 inhibitor, wherein Compound (I) is represented by the following structural formula:

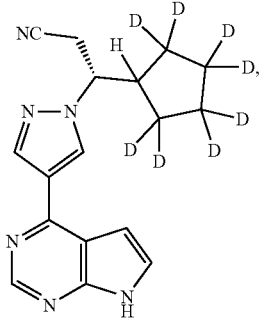

Compound (I)

or a pharmaceutically acceptable salt thereof, wherein each position designated specifically as deuterium has at least 95% incorporation of deuterium; and
wherein, the therapeutically effective amount of Compound (I), or a pharmaceutically acceptable salt thereof, is not reduced compared to the therapeutically effective amount of Compound (I), or pharmaceutically acceptable salt thereof, that would be administered to the subject in the absence of concomitant administration of a CYP3A4 inhibitor.

In a first aspect, for any one of the first through sixth embodiments, the JAK-inhibition-responsive condition is a hair loss disorder which is alopecia areata.

In a second aspect, for any one of the first through sixth embodiments or the first aspect thereof, Compound (I) or a pharmaceutically acceptable salt thereof, is administered in an amount in the range of about 8 mg to about 32 mg per day.

In a third aspect, for any one of the first through sixth embodiments or the first or second aspect thereof, Compound (I), or a pharmaceutically acceptable salt thereof, is administered at about 16 mg/day, or about 24 mg/day.

In a fourth aspect, for any one of the first through sixth embodiments or the first, second or third aspects thereof, the about 16 mg/day of Compound (I) or pharmaceutically acceptable salt thereof is administered as about 8 mg twice per day and the about 24 mg/day of the compound or pharmaceutically acceptable salt thereof is administered as about 12 mg twice per day.

In a fifth aspect, for any one of the first through sixth embodiment or the first or second aspects thereof the about 8 mg/day of Compound (I) or pharmaceutically acceptable slat thereof is administered as about 8 mg once per day or 4 mg twice per day.

In a sixth aspect, for any one of the first through sixth embodiments or the first, second, third, fourth or fifth aspects thereof, Compound (I) or a pharmaceutically acceptable salt thereof, is administered orally.

In a seventh aspect, for any one of the first through sixth embodiments or the first, second, third, fourth, fifth or sixth aspects thereof, Compound (I), or a pharmaceutically acceptable salt thereof, is administered in a pharmaceutical formulation which is a tablet.

In an eighth aspect, for any one of the first through sixth embodiments or the first, second, third, fourth, fifth, sixth or seventh aspects thereof, Compound (I), or a pharmaceutically acceptable salt thereof, is administered to the human subject for at least 24 weeks.

In a ninth aspect, for any one of the first through sixth embodiments or the first, second, third, fourth, fifth, sixth, seventh or eighth aspects thereof, in Compound (I), each position designated specifically as deuterium has at least 97% incorporation of deuterium.

In a tenth aspect, for any one of the first through sixth embodiments or the first, second, third, fourth, fifth, sixth, seventh, eighth or ninth aspects thereof, the human subject's SALT score is less than or equal to 20 after treatment.

In an eleventh aspect, for any one of the first through sixth embodiments or the first, second, third, fourth, fifth, sixth, seventh, eighth, ninth or tenth aspects thereof, the CYP3A4 inhibitor is a strong CYP3A4 inhibitor.

In an twelfth aspect, for any one of the first through sixth embodiments or the first, second, third, fourth, fifth, sixth, seventh, eighth, ninth or tenth aspects thereof, the CYP3A4 inhibitor is selected from boceprevir, cobicistat, danoprevir plus ritonavir, elvitegravir plus ritonavir, grapefruit juice, indinavir plus ritonavir, itraconazole, ketoconazole, lopinavir plus ritonavir, paritaprevir plus ritonavir plus (ombitasvir and/or dasabuvir), posaconazole, ritonavir, saquinavir plus ritonavir, telaprevir, tipranavir plus ritonavir, telithromycin, troleandomycin, voriconazole, clarithromycin, idelalisib, nefazodone and nelfinavir.

In a thirteenth aspect, for any one of the first through sixth embodiments or the first, second, third, fourth, fifth, sixth, seventh, eighth, ninth, tenth, eleventh or twelfth aspects thereof, no interruption of the administration of the CYP3A4 inhibitor is required.

In a seventh embodiment, the invention relates to a method of treating a hair loss disorder in a human subject in need thereof, wherein the human subject is concomitantly administered a strong CYP3A4 inhibitor, the method comprising administering to the human subject a therapeutically effective amount of Compound (I) represented by the following structural formula:

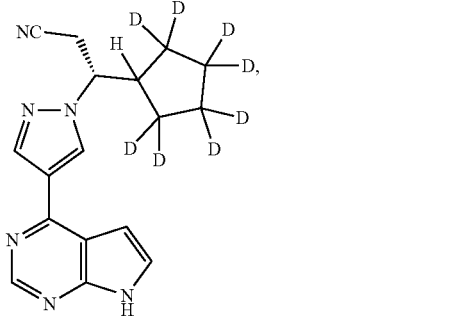

Compound (I)

or a pharmaceutically acceptable salt thereof, wherein each position designated specifically as deuterium has at least 95% incorporation of deuterium; and wherein: the therapeutically effective amount of Compound (I), or a pharmaceutically acceptable salt thereof, is not reduced compared to the therapeutically effective amount of Compound (I), or pharmaceutically acceptable salt thereof, that would be administered to the subject in the absence of concomitant administration of the strong CYP3A4 inhibitor.

In a first aspect of the seventh embodiment, the hair loss disorder is alopecia areata.

In a second aspect of the seventh embodiment or the first aspect thereof, Compound (I) or a pharmaceutically acceptable salt thereof, is administered in an amount in the range of about 8 mg to about 32 mg per day.

In a third aspect of the seventh embodiment or the first or second aspects thereof, Compound (I), or a pharmaceutically acceptable salt thereof, is administered at about 16 mg/day, or about 24 mg/day.

In a fourth aspect of the seventh embodiment or the first, second or third aspects thereof, the about 16 mg/day of Compound (I) or pharmaceutically acceptable salt thereof is administered as about 8 mg twice per day and the about 24 mg/day of the compound or pharmaceutically acceptable salt thereof is administered as about 12 mg twice per day.

In a fifth aspect, for any one of the first through sixth embodiment or the first or second aspects thereof the about 8 mg/day of Compound (I) or pharmaceutically acceptable slat thereof is administered as about 8 mg once per day or 4 mg twice per day.

In a sixth aspect, for any one of the first through sixth embodiments or the first, second, third, fourth or fifth aspects thereof, Compound (I) or a pharmaceutically acceptable salt thereof, is administered orally.

In a seventh aspect, for any one of the first through sixth embodiments or the first, second, third, fourth, fifth or sixth aspects thereof, Compound (I), or a pharmaceutically acceptable salt thereof, is administered in a pharmaceutical formulation which is a tablet.

In an eighth aspect, for any one of the first through sixth embodiments or the first, second, third, fourth, fifth, sixth or seventh aspects thereof, Compound (I), or a pharmaceutically acceptable salt thereof, is administered to the human subject for at least 24 weeks.

In a ninth aspect, for any one of the first through sixth embodiments or the first, second, third, fourth, fifth, sixth, seventh or eighth aspects thereof, in Compound (I), each position designated specifically as deuterium has at least 97% incorporation of deuterium.

In a tenth aspect, for any one of the first through sixth embodiments or the first, second, third, fourth, fifth, sixth, seventh, eighth or ninth aspects thereof, the human subject's SALT score is less than or equal to 20 after treatment.

In an eleventh aspect of the seventh embodiment or the first, second, third, fourth, fifth, sixth, seventh, eighth, ninth or tenth aspects thereof, no interruption of the administration of the CYP3A4 inhibitor is required.

DETAILED DESCRIPTION OF THE INVENTION

Definitions

Compound I

Compound I, as referred to herein, is (R)-3-(4-(7H-pyrrolo[2,3-d]pyrimidin-4-yl)-1H-pyrazol-1-yl)-3-(cyclopentyl-2,2,3,3,4,4,5,5-$d_8$)propanenitrile:

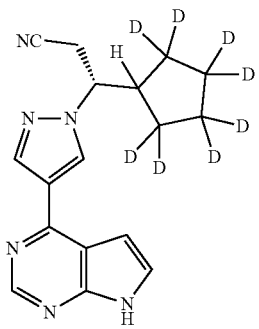

Compound I is also referred to herein as CTP-543 and is a potent selective inhibitor of Janus kinases JAK1 and JAK2. The compound is disclosed in International Patent Applications WO 2013/188783A1, WO 2017/192905A1 and WO2020/163653. CTP-543 is currently being investigated in human clinical trials and has been shown to stimulate hair growth in patients suffering from alopecia areata.

The synthesis of Compound (I), or a pharmaceutically acceptable salt thereof (such as the phosphate salt) may be readily achieved by the methods described U.S. Pat. No. 9,249,149, WO 2017/192905A1 and WO2020/163653, the teachings of all of which are incorporated herein by reference, with appropriate modifications, if needed. Additional methods of preparing ruxolitinib (i.e., the non-deuterated analog Compound (I)) are disclosed in U.S. Pat. No. 9,000,161, and can be used, with use of suitable deuterated reagents, to prepare Compound (I).

Such methods can be carried out utilizing corresponding deuterated and optionally, other isotope-containing reagents and/or intermediates to synthesize the compounds delineated herein, or invoking standard synthetic protocols known in the art for introducing isotopic atoms to a chemical structure.

As depicted above, Compound I is shown as a "free base". In some embodiments, a pharmaceutically acceptable salt of Compound (I) is used.

Pharmaceutically acceptable salts of Compound I include acid addition salts formed with inorganic acids or organic acids. Suitable inorganic acids include hydrochloric, hydrobromic, sulfuric and phosphoric acid. Suitable organic acids include paratoluenesulfonic, salicyclic, tartaric, ascorbic, maleic, besylic, fumaric, gluconic, glucuronic, formic, glutamic, methanesulfonic, ethanesulfonic, benzenesulfonic, lactic, oxalic, succinic, citric, benzoic and acetic acid. In certain embodiments, pharmaceutically acceptable salts of Compound (I) are selected from sulfate, phosphate, para-toluenesulfonate and methanesulfonate (mesylate) salts.

In certain embodiments, the pharmaceutically acceptable salt of Compound (I) is a phosphate salt. Conveniently, a phosphate salt of Compound I (in a 1:1 molar ratio) is used. The phosphate salt of Compound (I) I is depicted below:

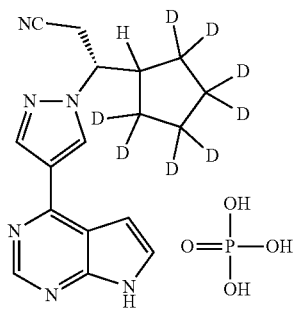

The molecular weight of Compound I is 314.2 g/mol. The molecular weight of the 1:1 phosphate salt of Compound (I) is 412.2 g/mol.

In an embodiment, the ratio of Compound I to phosphate in the salt form is about 1:1.

In one embodiment, any atom not designated as deuterium is present at its natural isotopic abundance in Compound (I), or a pharmaceutically acceptable salt thereof.

The pharmaceutically acceptable salt of Compound I may be present as a hydrate, solvate or in anhydrous form. In certain embodiments, the pharmaceutically acceptable salt is anhydrous. In a more specific embodiment, the phosphate salt is anhydrous.

Throughout the specification, unless specified otherwise, references to the amount of Compound I will be understood to refer to the amount of the parent compound on a free base basis, even if the compound is present as a salt of Compound I.

Purely by way of example, reference to 12 mg of Compound I or a salt thereof, will be understood to refer to 12 mg of the free base, or a salt of Compound I with 12 mg of free base equivalent. In the context of the anhydrous monophosphate salt of Compound (I), about 15.7 mg of the salt delivers 12 mg of Compound (I) (free base equivalent).

The synthesis of Compound I, or a pharmaceutically acceptable salt thereof (such as the phosphate salt) may be readily achieved by the methods described in WO2020/163653, the teachings of which are incorporated herein by reference.

CYP3A4 Inhibitors

The cytochrome P450 (CYP) is a well-known superfamily of enzymes that are responsible for the oxidative and reductive metabolic transformation of medications used in clinical practice. In addition, the CYP enzymes are commonly associated with causing many clinically relevant drug-drug interactions. Of the CYP enzymes, CYP3A4 is not only the most prevalent CYP enzyme in the liver, but is used by more than 50% of medications on the market for their metabolism and elimination from the body. In addition, the CYP3A4 activity can be induced (or accelerated) or it can be inhibited (decreased), thereby changing the drug concentrations present in the body and its pharmacokinetic profile. The inhibition of CYP3A4 can result in the accumulation of parent drug concentrations that can put the patient at increased risk for side effects and possible toxicity.

According to guidance from the U.S. FDA, strong, moderate, and weak inhibitors are drugs that increase the AUC of sensitive index substrates of a given metabolic pathway ≥5-fold, ≥2 to <5-fold, and ≥1.25 to <2-fold, respectively. The lists reproduced below are provided by the FDA (see: https://www.fda.gov/drugs/drug-interactions-labeling/drug-development-and-drug-interactions-table-substrates-inhibitors-and-inducerskable3-2). The list provided by the FDA is not exhaustive. As such, CYP3A4 inhibitors include, but are not limited to, the inhibitors listed below.

STRONG INHIBITORS: boceprevir, cobicistat, danoprevir plus ritonavir, elvitegravir plus ritonavir, grapefruit juice, indinavir plus ritonavir, itraconazole, ketoconazole, lopinavir plus ritonavir, paritaprevir plus ritonavir plus (ombitasvir and/or dasabuvir), posaconazole, ritonavir, saquinavir plus ritonavir, telaprevir, tipranavir plus ritonavir, telithromycin, troleandomycin, voriconazole, clarithromycin, idelalisib, nefazodone and nelfinavir.

MODERATE INHIBITORS: aprepitant, ciprofloxacin, conivaptan, crizotinib, cyclosporine, diltiazem, dronedarone, erythromycin, fluconazole, fluvoxamine, imatinib, tofisopam and verapamil.

WEAK INHIBITORS: chlorzoxazone, cilostazol, cimetidine, clotrimazole, fosaprepitant, istradefylline, ivacaftor, lomitapide, ranitidine, ranolazine and ticagrelor.

The term "treat" means decrease, suppress, attenuate, diminish, arrest, or stabilize the development or progression of a disease (e.g., a disease or disorder delineated herein), lessen the severity of the disease or improve the symptoms associated with the disease. For example, treatment of a hair loss disorder includes regrowth of hair, prevention of further hair loss, or diminishing the rate of hair loss.

The term "JAK-inhibition-responsive condition" refers to a disease or disorder in a mammalian (e.g., a human) subject that can be treated by inhibition of the activity of a JAK (JAK1 and/or JAK2)) in a mammalian (e.g. human) subject.

In certain embodiments, the "JAK-inhibition-responsive condition" includes, but is not limited to, diseases involving the immune system including, for example, organ transplant rejection (e.g., allograft refection and graft versus host disease); hair loss disorders such as alopecia (including alopecia areata (AA), alopecia totalis, alopecia universalis); autoimmune diseases such as multiple sclerosis, rheumatoid arthritis, juvenile arthritis, type I diabetes, lupus, psoriasis, inflammatory bowel disease, ulcerative colitis, Crohn's disease, myasthenia gravis, immunoglobulin nephropathies, autoimmune thyroid disorders; allergic conditions such as asthma, food allergies, atopic dermatitis and rhinitis; viral diseases such as Epstein Barr virus (EBV), hepatitis B, hepatitis C, HIV, HTLV 1, varicella-zoster virus (VZV) and human papilloma virus (HPV); skin disorders such as psoriasis (for example, psoriasis vulgaris), atopic dermatitis, hidradenitis suppurativa, skin rash, skin irritation, skin sensitization (e.g., contact dermatitis or allergic contact dermatitis) and vitiligo; cancer, including those characterized by solid tumors (e.g., prostate cancer, renal cancer, hepatic cancer, pancreatic cancer, gastric cancer, breast cancer, lung cancer, cancers of the head and neck, thyroid cancer, glioblastoma, Kaposi's sarcoma, Castleman's disease, melanoma), hematological cancers (e.g., lymphoma, leukemia such as acute lymphoblastic leukemia, or multiple myeloma), and skin cancer such as cutaneous T-cell lymphoma (CTCL) and cutaneous B-cell lymphoma (examples of which include Sezary syndrome and mycosis fungoides; myeloproliferative disorders (MPDS) such as polycythemia vera (PV), essential thrombocythemia (ET), myeloid metaplasia with myelofibrosis (MMM), chronic myelomonocytic leukemia (CMML), hypereosinophilic syndrome (HES), systemic mast cell disease (SMCD); inflammation and inflammatory diseases, such as inflammatory diseases of the eye (e.g., iritis, uveitis, scleritis, conjunctivitis, or related disease), inflammatory diseases of the respiratory tract (e.g., the upper respiratory tract including the nose and sinuses such as rhinitis or sinusitis or the lower respiratory tract including bronchitis, chronic obstructive pulmonary disease, and the like), inflammatory myopathy such as myocarditis; systemic inflammatory response syndrome (SIRS) and septic shock; ischemia reperfusion injuries or a disease or condition related to an inflammatory ischemic event such as stroke or cardiac arrest; anorexia; cachexia; fatigue such as that resulting from or associated with cancer; restenosis; sclerodermitis; fibrosis; conditions associated with hypoxia or astrogliosis such as, for example diabetic retinopathy, cancer or neurodegeneration; gout; increased prostate size due to, e.g., benign prostatic hypertrophy or benign prostatic hyperplasia and other hair loss disorders, such as androgenetic alopecia and telogen effluvium.

In certain embodiments, the "JAK-inhibition-responsive condition" includes, but is not limited to, diseases involving the immune system including, for example, organ transplant rejection (e.g., allograft refection and graft versus host disease); hair loss disorders such as alopecia (including alopecia areata (AA), alopecia totalis, alopecia universalis); autoimmune diseases such as multiple sclerosis, rheumatoid arthritis, juvenile arthritis, type I diabetes, lupus, psoriasis, inflammatory bowel disease, ulcerative colitis, Crohn's disease, myasthenia gravis, immunoglobulin nephropathies, autoimmune thyroid disorders; allergic conditions such as asthma, food allergies, atopic dermatitis and rhinitis; viral diseases such as Epstein Barr virus (EBV), hepatitis B, hepatitis C, HIV, HTLV 1, varicella-zoster virus (VZV) and human papilloma virus (HPV); skin disorders such as psoriasis (for example, psoriasis vulgaris), atopic dermatitis, hidradenitis suppurativa, skin rash, skin irritation and skin sensitization (e.g., contact dermatitis or allergic contact dermatitis); cancer, including those characterized by solid tumors (e.g., prostate cancer, renal cancer, hepatic cancer, pancreatic cancer, gastric cancer, breast cancer, lung cancer, cancers of the head and neck, thyroid cancer, glioblastoma, Kaposi's sarcoma, Castleman's disease, melanoma), hematological cancers (e.g., lymphoma, leukemia such as acute lymphoblastic leukemia, or multiple myeloma), and skin cancer such as cutaneous T-cell lymphoma (CTCL) and cutaneous B-cell lymphoma (examples of which include Sezary syndrome and mycosis fungoides; myeloproliferative disorders (MPDS) such as polycythemia vera (PV), essential thrombocythemia (ET), myeloid metaplasia with myelofibrosis (MMM), chronic myelomonocytic leukemia (CMML), hypereosinophilic syndrome (HES), systemic mast cell disease (SMCD); inflammation and inflammatory diseases, such as inflammatory diseases of the eye (e.g., iritis, uveitis, scleritis, conjunctivitis, or related disease), inflammatory diseases of the respiratory tract (e.g., the upper respiratory tract including the nose and sinuses such as rhinitis or sinusitis or the lower respiratory tract including bronchitis, chronic obstructive pulmonary disease, and the like), inflammatory myopathy such as myocarditis; systemic inflammatory response syndrome (SIRS) and septic shock; ischemia reperfusion injuries or a disease or condition related to an inflammatory ischemic event such as stroke or cardiac arrest; anorexia; cachexia; fatigue such as that resulting from or associated with cancer; restenosis; sclerodermitis; fibrosis; conditions associated with hypoxia or astrogliosis such as, for example diabetic retinopathy, cancer or neurodegeneration; gout; increased prostate size due to, e.g., benign prostatic hypertrophy or benign prostatic hyperplasia and other hair loss disorders, such as androgenetic alopecia and telogen effluvium.

In certain embodiments, the condition is selected from a hair loss disorder, polycythemia vera (PV), myelofibrosis (MF), or an acute Graft-versus-Host Disease (aGVHD). In certain embodiments, the JAK-inhibition-responsive condition is a hair loss disorder.

"Hair loss disorder" means any condition or disorder that results in loss of hair on one or more areas of the body. Hair loss disorders include, without limitation, androgenetic alopecia, alopecia areata, telogen effluvium, alopecia totalis, and alopecia universalis. In a specific embodiment the hair loss disorder is alopecia areata.

Alopecia areata is an autoimmune disease that results in partial or complete loss of hair on the scalp and body that may affect up to 650,000 Americans at any given time. The scalp is the most commonly affected area, but any hair-bearing site can be affected alone or together with the scalp. Onset of the disease can occur throughout life and affects both women and men. Alopecia areata can be associated with serious psychological consequences, including anxiety and depression. There are currently no drugs approved by the U.S. Food and Drug Administration (FDA) for the treatment of alopecia areata.

In a specific embodiment, the condition is alopecia areata in a subject such as a mammalian (e.g., human) patient in need thereof. In certain embodiments, the alopecia areata is moderate to severe alopecia areata (for example, hair loss over at least 30% of the scalp, hair loss over at least 40% of the scalp, or hair loss over at least 50% of the scalp).

The term "mammal", as used herein, includes humans, as well as non-human mammals such as cats, dogs, sheep, cattle, pigs, goats, non-human primates (including monkeys and apes) and the like.

The terms "concomitant" and "concomitantly" as used herein refers to the administration of at least two drugs to a subject wherein a second drug is administered either subsequently or simultaneously within a time period so that the effect of the first administered drug is still operating in the patient. For example, in some embodiments, concomitant administrations of the second drug (e.g., a CYP3A4 inhibitor) occurs within one day before or after administration of the first drug. As such, when a subject is described as receiving a concomitant administration of a CYP3A4 inhibitor, the subject may have already taken the CYP3A4 inhibitor or the subject may be planning to take (will take) the CYP3A4 inhibitor.

The language "not reduced compared to the therapeutically effective amount of Compound (I), or pharmaceutically acceptable salt thereof, that would be administered to the subject in the absence of concomitant administration of a CYP3A4 inhibitor" means that the dose of Compound (I) administered to a subject receiving concomitant treatment with a CYP3A4 inhibitor is the same dose that would be administered to the subject in the absence of treatment with the CYP3A4 inhibitor. For example, the dose that would be administered to the subject in the absence of treatment with the CYP3A4 inhibitor can be the dosage approved by the FDA or its counterpart foreign agency for treatment of the identified disease or condition.

It will be recognized that some variation of natural isotopic abundance occurs in a synthesized compound depending upon the origin of chemical materials used in the synthesis. Thus, a preparation of ruxolitinib will inherently contain small amounts of deuterated isotopologues. The concentration of naturally abundant stable hydrogen and carbon isotopes, notwithstanding this variation, is small and immaterial as compared to the degree of stable isotopic substitution of the deuterated compounds of this invention. See, for instance, Wada, E et al., Seikagaku, 1994, 66:15; Gannes, L Z et al., Comp Biochem Physiol Mol Integr Physiol, 1998, 119:725.

In any of the compounds described herein, for example Compound I, any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. However, in certain embodiments where stated, when a position is designated specifically as "H" or "hydrogen", the position has at least 80%, at least 90%, at least 95%, at least 96%, at least 97%, at least 98%, or at least 99% hydrogen. In some embodiments, where specifically stated, when a position is designated specifically as "H" or "hydrogen", the position incorporates ≤20% deuterium, ≤10% deuterium, ≤5% deuterium, ≤4% deuterium, ≤3% deuterium, ≤2% deuterium, or ≤1% deuterium. Also unless otherwise stated, when a position is designated specifically as "D" or "deuterium", the position is understood to have deuterium at an abundance that is at least 3340 times greater than the natural abundance of deuterium, which is 0.015% (i.e., at least 50.1% incorporation of deuterium). The amount of deuterium incorporation at a designated position may be measured by analytical methods known to one of ordinary skill in the art, for example, by proton NMR.

The term "isotopic enrichment factor" as used herein means the ratio between the isotopic abundance and the natural abundance of a specified isotope.

In other embodiments, a deuterated compound of this invention has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

In some embodiments, in a compound of this invention, each designated deuterium position (or atom) has deuterium incorporation of at least 52.5%. In some embodiments, in a compound of this invention, each designated deuterium position has deuterium incorporation of at least 60%. In some embodiments, in a compound of this invention, each designated deuterium position has deuterium incorporation of at least 67.5%. In some embodiments, in a compound of this invention, each designated deuterium position has deuterium incorporation of at least 75%. In some embodiments, in a compound of this invention, each designated deuterium position has deuterium incorporation of at least 80%. In some embodiments, in a compound of this invention, each designated deuterium position has deuterium incorporation of at least 85%. In some embodiments, in a compound of this invention, each designated deuterium position has deuterium incorporation of at least 90%. In some embodiments, in a compound of this invention, each designated deuterium position has deuterium incorporation of at least 95%. In some embodiments, in a compound of this invention, each designated deuterium position has deuterium incorporation of at least 97%. In some embodiments, in a compound of this invention, each designated deuterium position has deuterium incorporation of at least 98%. In some embodiments, in a compound of this invention, each designated deuterium position has deuterium incorporation of at least 99%. In some embodiments, in a compound of this invention, each designated deuterium position has deuterium incorporation of at least 99.5%.

The term "isotopologue" refers to a species in which the chemical structure differs from any of the compounds described herein only in the isotopic composition thereof.

The term "compound," when referring to a deuterated compound of this invention, for example Compound I, refers to a collection of molecules having an identical chemical structure, except that there may be isotopic variation among the constituent atoms of the molecules. Thus, it will be clear to those of skill in the art that a compound represented by a particular chemical structure containing indicated deuterium atoms, will also contain isotopologues having hydrogen atoms at one or more of the designated deuterium positions in that structure. The relative amount of such isotopologues in a compound of this invention will depend upon a number of factors including the isotopic purity of deuterated reagents used to make the compound and the efficiency of incorporation of deuterium in the various synthesis steps used to prepare the compound. In certain embodiments, the relative amount of such isotopologues in toto will be less than 49.9% of the compound. In other embodiments, the relative amount of such isotopologues in toto will be less than 47.5%, less than 40%, less than 32.5%, less than 25%, less than 17.5%, less than 10%, less than 5%, less than 3%, less than 1%, or less than 0.5% of the compound.

The invention also provides salts of Compound I. A salt of a compound of this invention is formed between an acid and a basic group of the compound, such as an amino functional group, or a base and an acidic group of the compound, such as a carboxyl functional group. According to another embodiment, the compound is a pharmaceutically acceptable acid addition salt, such as a phosphate salt.

The term "pharmaceutically acceptable," as used herein, refers to a component that is, within the scope of sound medical judgment, suitable for use in contact with the tissues of humans and other mammals without undue toxicity, irritation, allergic response and the like, and are commensurate with a reasonable benefit/risk ratio. A "pharmaceutically acceptable salt" means any non-toxic salt that, upon administration to a recipient, is capable of providing, either directly or indirectly, a compound of this invention. A "pharmaceutically acceptable counterion" is an ionic portion of a salt that is not toxic when released from the salt upon administration to a recipient.

Acids commonly employed to form pharmaceutically acceptable salts include inorganic acids such as hydrogen bisulfide, hydrochloric acid, hydrobromic acid, hydroiodic acid, sulfuric acid and phosphoric acid, as well as organic acids such as para-toluenesulfonic acid, salicylic acid, tartaric acid, bitartaric acid, ascorbic acid, maleic acid, besylic acid, fumaric acid, gluconic acid, glucuronic acid, formic acid, glutamic acid, methanesulfonic acid, ethanesulfonic acid, benzenesulfonic acid, lactic acid, oxalic acid, para-bromophenylsulfonic acid, carbonic acid, succinic acid, citric acid, benzoic acid and acetic acid, as well as related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephthalate, sulfonate, xylene sulfonate, phenylacetate, phenylpropionate, phenylbutyrate, citrate, lactate, f3-hydroxybutyrate, glycolate, maleate, tartrate, methanesulfonate, propanesulfonate, naphthalene-1-sulfonate, naphthalene-2-sulfonate, mandelate and other salts. In one embodiment, pharmaceutically acceptable acid addition salts include those formed with mineral acids such as hydrochloric acid and hydrobromic acid, and especially those formed with organic acids such as maleic acid.

The term "stable compounds," as used herein, refers to compounds which possess stability sufficient to allow for their manufacture and which maintain the integrity of the compound for a sufficient period of time to be useful for the purposes detailed herein (e.g., formulation into therapeutic products, intermediates for use in production of therapeutic compounds, isolatable or storable intermediate compounds, treating a disease or condition responsive to therapeutic agents).

"D" and "d" both refer to deuterium. "Stereoisomer" refers to both enantiomers and diastereomers. "Tert" and "t-" each refer to tertiary. "US" refers to the United States of America.

"Substituted with deuterium" refers to the replacement of one or more hydrogen atoms with a corresponding number of deuterium atoms.

The term "treat" means decrease, suppress, attenuate, diminish, arrest, or stabilize the development or progression of a disease (e.g., a disease or disorder delineated herein), lessen the severity of the disease or improve the symptoms associated with the disease. For example, treatment of a hair loss disorder includes regrowth of hair, prevention of further hair loss, or diminishing the rate of hair loss.

The term "mammal", as used herein, includes humans, as well as non-human mammals such as cats, dogs, sheep, cattle, pigs, goats, non-human primates (including monkeys and apes) and the like.

As used herein, a "therapeutically effective amount" is an amount sufficient to treat the target condition or disorder. Where a drug has been approved by the U.S. Food and Drug Administration (FDA), a "therapeutically effective amount" can be the dosage approved by the FDA or its counterpart foreign agency for treatment of the identified disease or condition.

Dosing of Compound (I):

In certain embodiments, Compound (I) is administered as a pharmaceutically acceptable salt, such as the phosphate salt. Compound (I) can be administered in doses in the range of about 4 mg to about 50 mg per day (or the equivalent weight based on a salt, such as Compound (I) phosphate salt), administered as a single daily dose or in divided doses (e.g., twice per day).

One aspect of the method described herein for treating hair loss disorders comprises administering to a subject (e.g., a mammalian subject receiving a concomitant administration of a CYP3A4 inhibitor) a therapeutically effective amount of Compound (I), or a pharmaceutically acceptable salt thereof (i.e., an equivalent amount of a pharmaceutically acceptable salt, such as the phosphate salt)), once or twice per day, wherein the amount of Compound (I), or a pharmaceutically acceptable salt thereof, is in the range of about 4 mg/day to about 50 mg/day, for example, about 5 mg/day, about 10 mg/day, about 20 mg/day, about 30 mg/day, about 40 mg/day, or about 50 mg/day. In certain embodiments, the amount of Compound (I), or a pharmaceutically acceptable salt thereof, is about 4 mg/day, 8 mg/day, 16 mg/day, 32 mg/day or 48 mg/day. In certain embodiments, the amount of Compound (I), or a pharmaceutically acceptable salt thereof, is 8 mg/day, 16 mg/day, 24 mg/day, or 32 mg/day. In certain embodiments, the amount of Compound (I), or a pharmaceutically acceptable salt thereof, is 8 mg/day, 16 mg/day, 24 mg/day, or 32 mg/day. In certain embodiments, the amount of Compound (I), or a pharmaceutically acceptable salt thereof is 4 mg, 8 mg, 12 mg or 16 mg twice per day. In certain embodiments, the hair loss disorder is alopecia areata. In certain embodiments, the subject is a human. In a particular embodiment, Compound (I), or a pharmaceutically acceptable salt thereof (such as the phosphate salt), is administered orally at any of the foregoing dosages. In another particular embodiment, the Compound (I), or a pharmaceutically acceptable salt thereof, is administered orally at any of the foregoing dosages in a pharmaceutical formulation which is a tablet.

In an alternative aspect, the invention described herein provides a method for treating hair loss disorders, the method comprising topically administering to a subject (e.g., a mammalian subject receiving a concomitant administration of a CYP3A4 inhibitor) a therapeutically effective amount of Compound (I), or a pharmaceutically acceptable salt thereof (i.e., an equivalent amount of a pharmaceutically acceptable salt, such as the phosphate salt). In certain embodiments, the compound is administered in a pharmaceutical composition which is formulated for topical administration, such as a cream, ointment, lotion, foam or the like.

In another aspect, the invention provides a method for inducing hair growth in a subject. The method comprises administering to a mammalian subject receiving a concomitant administration of a CYP3A4 inhibitor a therapeutically effective amount of Compound (I), or a pharmaceutically acceptable salt thereof (i.e., an equivalent amount of a pharmaceutically acceptable salt, such as the phosphate salt), once or twice per day, wherein the amount of Compound (I), or a pharmaceutically acceptable salt thereof, is in the range of about 4 mg/day to about 50 mg/day, for example, about 5 mg/day, about 10 mg/day, about 20 mg/day, about 30 mg/day, about 40 mg/day, or about 50 mg/day. In certain embodiments, the amount of Compound (I), or a pharmaceutically acceptable salt thereof, is about 4 mg/day, 8 mg/day, 16 mg/day, 32 mg/day or 48 mg/day. In certain embodiments, the amount of Compound (I), or a pharmaceutically acceptable salt thereof, is 8 mg/day, 16 mg/day, 24 mg/day, or 32 mg/day.

In certain embodiments, the subject suffering from a hair loss disorder is suffering from alopecia areata. In certain embodiments, the subject is a human. In one embodiment, the subject is a human 6 years of age or older. Preferably, Compound (I), or a pharmaceutically acceptable salt thereof (such as the phosphate salt), is administered orally at any of the foregoing dosages. Preferably, the Compound (I), or a pharmaceutically acceptable salt thereof, is administered orally at any of the foregoing dosages in a pharmaceutical formulation which is a tablet.

Another aspect of the invention is a method for treating autoimmune skin disorders disorders that can be treated by compounds that modulate the activity of Janus Associated Kinase 1 (JAK1) and/or Janus Associated Kinase 2 (JAK2). The method comprises administering to a subject (e.g., a mammalian subject receiving a concomitant administration of a CYP3A4 inhibitor) a therapeutically effective amount of Compound (I), or a pharmaceutically acceptable salt thereof (i.e., an equivalent amount of a pharmaceutically acceptable salt, such as the phosphate salt), once or twice per day, wherein the amount of Compound (I), or a pharmaceutically acceptable salt thereof, is in the range of about 4 mg/day to about 50 mg/day, for example, about 5 mg/day, about 10 mg/day, about 20 mg/day, about 30 mg/day, about 40 mg/day, or about 50 mg/day. In certain embodiments, the amount of Compound (I), or a pharmaceutically acceptable salt thereof, is about 4 mg/day, 8 mg/day, 16 mg/day, 32 mg/day or 48 mg/day. In certain embodiments, the amount of Compound (I), or a pharmaceutically acceptable salt thereof, is 8 mg/day, 16 mg/day, 24 mg/day, or 32 mg/day. In certain embodiments, the amount of Compound (I), or a pharmaceutically acceptable salt thereof, is 8 mg/day, 16 mg/day, 24 mg/day, or 32 mg/day. In certain embodiments, the amount of Compound (I), or a pharmaceutically acceptable salt thereof is 4 mg, 8 mg, 12 mg or 16 mg twice per day. In certain embodiments, the autoimmune skin disorder is alopecia areata, vitiligo, atopic dermatitis (ezcema), or psoriasis. In certain embodiments, the subject is a human. Preferably, Compound (I), or a pharmaceutically acceptable salt thereof (such as the phosphate salt), is administered orally at any of the foregoing dosages. Preferably, the Compound (I), or a pharmaceutically acceptable salt thereof, is administered orally at any of the foregoing dosages in a pharmaceutical formulation which is a tablet.

Another aspect of the invention is Compound (I), or a pharmaceutically acceptable salt thereof (i.e., an equivalent amount of a pharmaceutically acceptable salt, such as the phosphate salt), for use in treating hair loss disorders that can be treated by compounds that modulate the activity of Janus kinase 1 (JAK1) and/or Janus kinase 2 (JAK2). The compound may be administered at the dosing regimens disclosed herein. In certain embodiments, the hair loss disorder is alopecia areata.

In one aspect, the invention provides a method for treating hair loss disorders that can be treated by compounds that modulate (e.g., inhibit) the activity of a JAK (e.g., JAK1 and/or JAK2). The method comprises administering to a mammalian subject a therapeutically effective amount of Compound (I), or a pharmaceutically acceptable salt thereof (i.e., an equivalent amount of a pharmaceutically acceptable salt, such as the phosphate salt), once or twice per day, wherein the amount of Compound (I), or a pharmaceutically acceptable salt thereof, is in the range of about 4 mg/day to about 50 mg/day (such as 4 mg/day to 50 mg/day), for example, about 5 mg/day (such as 5 mg/day), about 10 mg/day (such as 10 mg/day), about 20 mg/day (such as 20 mg/day), about 30 mg/day (such as 30 mg/day), about 40 mg/day (such as 40 mg/day), or about 50 mg/day (such as 50 mg/day).

In certain embodiments, the amount of Compound (I), or a pharmaceutically acceptable salt thereof (i.e., an equivalent amount of a pharmaceutically acceptable salt, such as the phosphate salt) administered in the method for treating hair loss disorders, is about 4 mg/day (such as 4 mg/day), about 8 mg/day (such as 8 mg/day), about 16 mg/day (such as 16 mg/day), about 32 mg/day (such as 32 mg/day) or about 48 mg/day (such as 48 mg/day).

In certain embodiments, the amount of Compound (I), or a pharmaceutically acceptable salt thereof administered in the method for treating hair loss disorders, is about 8 mg/day (such as 8 mg/day), about 16 mg/day (such as 16 mg/day), about 24 mg/day (such as 24 mg/day), or about 32 mg/day (such as 32 mg/day). In certain embodiments, the amount of Compound (I), or a pharmaceutically acceptable salt thereof, is about 8 mg/day (such as 8 mg/day), about 12 mg/day (such as 12 mg/day), about 16 mg/day (such as 16 mg/day) or about 24 mg/day (such as 24 mg/day).

In certain embodiments, the amount of Compound (I), or a pharmaceutically acceptable salt thereof administered in the method for treating hair loss disorders, is 10.6 mg/day of Compound (I) phosphate, e.g., administered as a 5.3 mg dose twice daily. In certain embodiments, the amount of Compound (I), or a pharmaceutically acceptable salt thereof, is 21.1 mg/day of Compound (I) phosphate, e.g., administered as a 10.5 mg dose twice daily. In certain embodiments, the amount of Compound (I), or a pharmaceutically acceptable salt thereof, is 31.6 mg/day of Compound (I) phosphate, e.g., administered as a 15.8 mg dose twice daily. In certain embodiments, the amount of Compound (I), or a pharmaceutically acceptable salt thereof, is 42.2 mg/day of Compound (I) phosphate, e.g., administered as a 21.1 mg dose twice daily.

In certain embodiments, the amount of Compound (I), or a pharmaceutically acceptable salt thereof administered in the method for treating hair loss disorders is about 4 mg (such as 4 mg) twice per day. In a specific embodiment, Compound (I) is administered as about 5.3 mg (such as 5.3 mg) of the phosphate salt of Compound (I) twice per day. In certain embodiments, the amount of Compound (I), or a pharmaceutically acceptable salt thereof administered in the method for treating hair loss disorders is about 8 mg (such as 8 mg) twice per day. In a specific embodiment, Compound (I) is administered as about 10.5 mg (such as 10.5 mg) of the phosphate salt of Compound (I) twice per day.

In certain embodiments, the amount of Compound (I), or a pharmaceutically acceptable salt thereof administered in the method for treating hair loss disorders is about 12 mg (such as 12 mg) twice per day. In a specific embodiment, Compound (I) is administered as about 15.8 mg (such as 15.8 mg) of the phosphate salt of Compound (I) twice per day. In certain embodiments, the amount of Compound (I), or a pharmaceutically acceptable salt thereof administered in the method for treating hair loss disorders is about 16 mg (such as 16 mg) twice per day. In a specific embodiment, Compound (I) is administered as about 21.1 mg (such as 21.1 mg) of the phosphate salt of Compound (I) twice per day. In certain embodiments, the hair loss disorder is alopecia areata. In certain embodiments, the subject is a human. In one embodiment, the subject is a human 6 years of age or older. Preferably, Compound (I), or a pharmaceutically acceptable salt thereof (such as the phosphate salt), is administered orally at any of the dosages described herein. Preferably, the Compound (I), or a pharmaceutically acceptable salt thereof, is administered orally at any of the dosages described herein in a pharmaceutical formulation which is a tablet.

In another aspect, the invention provides a method for inducing hair growth in a subject. The method comprises administering to a mammalian subject a therapeutically effective amount of Compound (I), or a pharmaceutically acceptable salt thereof (i.e., an equivalent amount of a pharmaceutically acceptable salt, such as the phosphate salt), once or twice per day, wherein the amount of Compound (I), or a pharmaceutically acceptable salt thereof, is in the range of about 4 mg/day to about 50 mg/day (such as 4 mg/day to 50 mg/day), for example, about 5 mg/day (such as 5 mg/day), about 10 mg/day (such as 10 mg/day), about 20 mg/day (such as 20 mg/day), about 30 mg/day (such as 30 mg/day), about 40 mg/day (such as 40 mg/day), or about 50 mg/day (such as 50 mg/day).

In certain embodiments, the amount of Compound (I), or a pharmaceutically acceptable salt thereof administered in the method for inducing hair growth, is about 4 mg/day (such as 4 mg/day), about 8 mg/day (such as 8 mg/day), about 16 mg/day (such as 16 mg/day), about 32 mg/day (such as 32 mg/day) or about 48 mg/day (such as 48 mg/day).

In certain embodiments, the amount of Compound (I), or a pharmaceutically acceptable salt thereof administered in the method for inducing hair growth, is about 8 mg/day (such as 8 mg/day), about 16 mg/day (such as 16 mg/day), about 24 mg/day (such as 24 mg/day), or about 32 mg/day (such as 32 mg/day). In certain embodiments, the amount of Compound (I), or a pharmaceutically acceptable salt thereof administered in the method for inducing hair growth, is about 8 mg/day (such as 8 mg/day), about 12 mg/day (such as 12/mg/day), about 16 mg/day (such as 16 mg/day), or about 24 mg/day (such as 24 mg/day).

In certain embodiments, the amount of Compound (I), or a pharmaceutically acceptable salt thereof administered in the method for inducing hair growth, is 10.6 mg/day of Compound (I) phosphate, e.g., administered as a 5.3 mg dose twice daily. In certain embodiments, the amount of Compound (I), or a pharmaceutically acceptable salt thereof, is 21.1 mg/day of Compound (I) phosphate, e.g., administered as a 10.5 mg dose twice daily. In certain embodiments, the amount of Compound (I), or a pharmaceutically acceptable salt thereof, is 31.6 mg/day of Compound (I) phosphate, e.g., administered as a 15.8 mg dose twice daily. In certain embodiments, the amount of Compound (I), or a pharmaceutically acceptable salt thereof, is 42.2 mg/day of Compound (I) phosphate, e.g., administered as a 21.1 mg dose twice daily.

In certain embodiments, the amount of Compound (I), or a pharmaceutically acceptable salt thereof administered in the method for inducing hair growth is about 4 mg (such as 4 mg) twice per day. In a specific embodiment, Compound (I) is administered as about 5.3 mg (such as 5.3 mg) of the phosphate salt of Compound (I) twice per day.

In certain embodiments, the amount of Compound (I), or a pharmaceutically acceptable salt thereof administered in the method for inducing hair growth is about 8 mg (such as 8 mg) twice per day. In a specific embodiment, Compound (I) is administered as about 10.5 mg (such as 10.5 mg) of the phosphate salt of Compound (I) twice per day.

In certain embodiments, the amount of Compound (I), or a pharmaceutically acceptable salt thereof administered in the method for inducing hair growth is about 12 mg (such as 12 mg) twice per day. In a specific embodiment, Compound (I) is administered as the about 15.8 mg (such as 15.8 mg) of the phosphate salt of Compound (I) twice per day.

In certain embodiments, the amount of Compound (I), or a pharmaceutically acceptable salt thereof administered in the method for inducing hair growth is about 16 mg (such as 16 mg) twice per day. In a specific embodiment, Compound (I) is administered as the about 21.1 mg (such as 21.1 mg) of the phosphate salt of Compound (I) twice per day.

In certain embodiments, the subject suffers from a hair loss disorder; in further embodiments, the hair loss disorder is alopecia areata. In certain embodiments, the subject is a human. In one embodiment, the subject is a human 6 years of age or older. Preferably, Compound (I), or a pharmaceutically acceptable salt thereof (such as the phosphate salt), is administered orally at any of the foregoing dosages. Preferably, the Compound (I), or a pharmaceutically acceptable salt thereof, is administered orally at any of the foregoing dosages in a pharmaceutical formulation which is a tablet.

One aspect of the method described herein for treating a JAK-inhibition-responsive condition comprises administering to a subject (e.g., a mammalian subject receiving a concomitant administration of a CYP3A4 inhibitor) a therapeutically effective amount of Compound (I), or a pharmaceutically acceptable salt thereof (i.e., an equivalent amount of a pharmaceutically acceptable salt, such as the phosphate salt)), once or twice per day, wherein the amount of Compound (I), or a pharmaceutically acceptable salt thereof, is in the range of about 4 mg/day to about 50 mg/day, for example, about 5 mg/day, about 10 mg/day, about 20 mg/day, about 30 mg/day, about 40 mg/day, or about 50 mg/day. In certain embodiments, the amount of Compound (I), or a pharmaceutically acceptable salt thereof, is about 4 mg/day, 8 mg/day, 16 mg/day, 32 mg/day or 48 mg/day. In certain embodiments, the amount of Compound (I), or a pharmaceutically acceptable salt thereof, is 8 mg/day, 16 mg/day, 24 mg/day, or 32 mg/day. In certain embodiments, the amount of Compound (I), or a pharmaceutically acceptable salt thereof, is 8 mg/day, 16 mg/day, 24 mg/day, or 32 mg/day. In certain embodiments, the amount of Compound (I), or a pharmaceutically acceptable salt thereof is 4 mg, 8 mg, 12 mg or 16 mg twice per day. In certain embodiments, the JAK-inhibition-responsive condition is alopecia areata. In certain embodiments, the subject is a human. In a particular embodiment, Compound (I), or a pharmaceutically acceptable salt thereof (such as the phosphate salt), is administered orally at any of the foregoing dosages. In another particular embodiment, the Compound (I), or a pharmaceutically acceptable salt thereof, is administered orally at any of the foregoing dosages in a pharmaceutical formulation which is a tablet.

Another aspect of the invention is Compound (I), or a pharmaceutically acceptable salt thereof (i.e., an equivalent amount of a pharmaceutically acceptable salt, such as the phosphate salt), for use in treating a JAK-inhibition-responsive condition. The compound may be administered at the dosing regimens disclosed herein.

In one aspect, the invention provides a method for treating a JAK-inhibition-responsive condition. The method comprises administering to a mammalian subject a therapeutically effective amount of Compound (I), or a pharmaceutically acceptable salt thereof (i.e., an equivalent amount of a pharmaceutically acceptable salt, such as the phosphate salt), once or twice per day, wherein the amount of Compound (I), or a pharmaceutically acceptable salt thereof, is in the range of about 4 mg/day to about 50 mg/day (such as 4 mg/day to 50 mg/day), for example, about 5 mg/day (such as 5 mg/day), about 10 mg/day (such as 10 mg/day), about 20 mg/day (such as 20 mg/day), about 30 mg/day (such as 30 mg/day), about 40 mg/day (such as 40 mg/day), or about 50 mg/day (such as 50 mg/day).

In certain embodiments, the amount of Compound (I), or a pharmaceutically acceptable salt thereof (i.e., an equivalent amount of a pharmaceutically acceptable salt, such as the phosphate salt) administered in the method for treating a JAK-inhibition-responsive condition, is about 4 mg/day (such as 4 mg/day), about 8 mg/day (such as 8 mg/day), about 16 mg/day (such as 16 mg/day), about 32 mg/day (such as 32 mg/day) or about 48 mg/day (such as 48 mg/day).

In certain embodiments, the amount of Compound (I), or a pharmaceutically acceptable salt thereof administered in the method for treating a JAK-inhibition-responsive condition, is about 8 mg/day (such as 8 mg/day), about 16 mg/day (such as 16 mg/day), about 24 mg/day (such as 24 mg/day), or about 32 mg/day (such as 32 mg/day). In certain embodiments, the amount of Compound (I), or a pharmaceutically acceptable salt thereof, is about 8 mg/day (such as 8 mg/day), about 12 mg/day (such as 12 mg/day), about 16 mg/day (such as 16 mg/day) or about 24 mg/day (such as 24 mg/day).

In certain embodiments, the amount of Compound (I), or a pharmaceutically acceptable salt thereof administered in the method for treating a JAK-inhibition-responsive condition, is 10.6 mg/day of Compound (I) phosphate, e.g., administered as a 5.3 mg dose twice daily. In certain embodiments, the amount of Compound (I), or a pharmaceutically acceptable salt thereof, is 21.1 mg/day of Compound (I) phosphate, e.g., administered as a 10.5 mg dose twice daily. In certain embodiments, the amount of Compound (I), or a pharmaceutically acceptable salt thereof, is 31.6 mg/day of Compound (I) phosphate, e.g., administered as a 15.8 mg dose twice daily. In certain embodiments, the amount of Compound (I), or a pharmaceutically acceptable salt thereof, is 42.2 mg/day of Compound (I) phosphate, e.g., administered as a 21.1 mg dose twice daily.

In certain embodiments, the amount of Compound (I), or a pharmaceutically acceptable salt thereof administered in the method for treating a JAK-inhibition-responsive condition is about 4 mg (such as 4 mg) twice per day. In a specific embodiment, Compound (I) is administered as about 5.3 mg (such as 5.3 mg) of the phosphate salt of Compound (I) twice per day. In certain embodiments, the amount of Compound (I), or a pharmaceutically acceptable salt thereof administered in the method for treating hair loss disorders is about 8 mg (such as 8 mg) twice per day. In a specific embodiment, Compound (I) is administered as about 10.5 mg (such as 10.5 mg) of the phosphate salt of Compound (I) twice per day.

In certain embodiments, the amount of Compound (I), or a pharmaceutically acceptable salt thereof administered in the method for treating a JAK-inhibition-responsive condition is about 12 mg (such as 12 mg) twice per day. In a specific embodiment, Compound (I) is administered as about 15.8 mg (such as 15.8 mg) of the phosphate salt of Compound (I) twice per day. In certain embodiments, the amount of Compound (I), or a pharmaceutically acceptable salt thereof administered in the method for treating hair loss disorders is about 16 mg (such as 16 mg) twice per day. In a specific embodiment, Compound (I) is administered as about 21.1 mg (such as 21.1 mg) of the phosphate salt of Compound (I) twice per day. In certain embodiments, the JAK-inhibition-responsive condition is alopecia areata.

In certain embodiments, the subject is a human. In one embodiment, the subject is a human 6 years of age or older. Preferably, Compound (I), or a pharmaceutically acceptable salt thereof (such as the phosphate salt), is administered orally at any of the dosages described herein. Preferably, the Compound (I), or a pharmaceutically acceptable salt thereof, is administered orally at any of the dosages described herein in a pharmaceutical formulation which is a tablet.

In one embodiment of any aspect, the compound is administered orally once a day. In other embodiments of any aspect, the compound is administered orally twice per day.

Effective doses will also vary, as recognized by those skilled in the art, depending on the diseases treated, the severity of the disease, the route of administration, the sex, age and general health condition of the subject, excipient usage, the possibility of co-usage with other therapeutic treatments such as use of other agents and the judgment of the treating physician.

The administration of Compound (I), or a pharmaceutically acceptable salt thereof (such as the phosphate salt), can continue for as long as necessary to treat a hair loss disorder, e.g., for one week, two weeks, one month, two months, three months, four months, six months, one year, two years, five years, ten years, or longer.

Methods of Assessing Treatment Efficacy:

The efficacy of treatment of hair loss disorders such as alopecia areata can be measured in a variety of ways, some of which are known in the art. For example, the "severity of alopecia tool", otherwise known as SALT, is a validated assessment scale—developed by the National Alopecia Areata Foundation working committee—to evaluate the degree of hair loss. See, e.g., Olsen E A, Hordinsky M K, Price V H, et al. Alopecia areata investigational assessment guidelines—Part II. J Am Acad Dermatol 2004: 51: 440-447 (incorporated herein by reference). The SALT score is calculated for a patient by measuring the percentage of hair loss in each of the 4 areas of the scalp and adding the total to achieve a composite score. Hair regrowth is reflected by a decrease in the SALT score. For example, no hair on the scalp would have a SALT score of 100 while complete hair regrowth would be a SALT score of 0. In certain embodiments, methods of treatment as described herein can provide a SALT score improvement of at least 10 points after treatment (for example, from a SALT score of 100 prior to treatment to a SALT score of 90 after treatment). In further embodiments, methods of treatment as described herein can provide a SALT score improvement of at least 20 points, 30 points, 40 points, 50 points, 60 points, 70 points, 80 points, 90 points, or 100 points. In certain embodiments, methods of treatment as described herein can provide after treatment at least a 20% improvement from baseline in the patient's SALT score, or at least a 30% improvement from baseline in the patient's SALT score, or at least a 40% improvement from baseline in the patient's SALT score, or at least a 50% improvement from baseline in the patient's SALT score, or at least a 60% improvement from baseline in the patient's SALT score, or at least a 70% improvement from baseline in the patient's SALT score.

In a particular embodiment, the human subject's SALT score is less than or equal to 20 after treatment (e.g., following at least four weeks of treatment, or at least 8 weeks of treatment, or at least 12 weeks of treatment, or at least 16 weeks of treatment, or at least 20 weeks of treatment, or at least 24 weeks of treatment, or at least 28 weeks of treatment, or at least 32 weeks of treatment, or at least 36 weeks of treatment, or at least 40 weeks of treatment, or at least 44 weeks of treatment, or at least 48 weeks of treatment, at least 52 weeks or longer.

In certain embodiments, treatment is continued for a period of at least four weeks, or at least 8 weeks, or at least 12 weeks, or at least 16 weeks, or at least 20 weeks, or at least 24 weeks, or at least 28 weeks, or at least 32 weeks, or at least 36 weeks, or at least 40 weeks, or at least 44 weeks, or at least 48 weeks, or at least 52 weeks.

Combination Therapy

In certain embodiments, Compound (I), or a pharmaceutically acceptable salt thereof, is administered in combination with a second therapeutic agent. Preferably, the second therapeutic agent is an agent useful in the treatment of hair loss disorders or autoimmune conditions, such as inhibitors of JAK1 or JAK2, or JAK3, and/or STAT1. Such inhibitors include ruxolitinib, tofacitinib, baricitinib, filgotinib, and the like. Other orally administered second therapeutic agents include agents used in the treatment of alopecia areata, including, for example, oral corticosteroids.

For pharmaceutical compositions that comprise a second therapeutic agent, a therapeutically effective amount of the second therapeutic agent is between about 20% and 100% of the dosage normally utilized in a monotherapy regime using just that agent. Preferably, a therapeutically effective amount is between about 70% and 100% of the normal monotherapeutic dose. The normal monotherapeutic dosages of these second therapeutic agents are well known in the art. See, e.g., Wells et al., eds., Pharmacotherapy Handbook, 2nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000); the FDA-approved labeling information for ruxolitinib and tofacitinib; and clinical trial information for baricitinib and filgotinib, each of which references are incorporated herein by reference in their entirety.

It is expected that some of the second therapeutic agents referenced above will act synergistically with the compounds of this invention. When this occurs, it will allow the effective dosage of the second therapeutic agent and/or Compound (I), or a pharmaceutically acceptable salt thereof, to be reduced from that required in a monotherapy. This has the advantage of minimizing toxic side effects of either the second therapeutic agent or Compound (I), or a pharmaceutically acceptable salt thereof, synergistic improvements in efficacy, improved ease of administration or use and/or reduced overall expense of compound preparation or formulation.

In another embodiment, any of the above methods of treatment comprises the further step of co-administering to the subject in need thereof one or more second therapeutic agents. The choice of second therapeutic agent may be made from any second therapeutic agent known to be useful for treatment of hair loss disorders such as alopecia areata. The choice of second therapeutic agent is also dependent upon the particular disease or condition to be treated. Examples of second therapeutic agents that may be employed in the methods of this invention are those set forth above for use in combination compositions comprising Compound (I), or a pharmaceutically acceptable salt thereof, and a second therapeutic agent. Additional therapeutic agents include agents used in the treatment of alopecia areata, including, for example, topical minoxidil, injected corticosteroids, and anthralin cream or ointment.

The term "co-administered" as used herein means that the second therapeutic agent may be administered together with Compound (I) or a pharmaceutically acceptable salt thereof, as part of a single dosage form (such as a composition of this invention comprising a compound of the invention and a second therapeutic agent as described above) or as separate, multiple dosage forms. Alternatively, the additional agent may be administered prior to, consecutively with, or following the administration of Compound (I), or a pharmaceutically acceptable salt thereof. In such combination therapy treatment, both Compound (I), or a pharmaceutically acceptable salt thereof, and the second therapeutic agent(s) are administered by conventional methods. The administration of a composition of this invention, comprising both Compound (I), or a pharmaceutically acceptable salt thereof, and a second therapeutic agent, to a subject does not preclude the separate administration of that same therapeutic agent, any other second therapeutic agent or Compound (I), or a pharmaceutically acceptable salt thereof, to said subject at another time during a course of treatment.

Therapeutically effective amounts of these second therapeutic agents are well known to those skilled in the art and guidance for dosing may be found in patents and published patent applications referenced herein, as well as in Wells et al., eds., Pharmacotherapy Handbook, 2nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), and other medical texts. However, it is well within the skilled artisan's purview to determine the second therapeutic agent's optimal effective-amount range.

In one embodiment of the invention, where a second therapeutic agent is administered to a subject, the therapeutically effective amount of Compound (I), or a pharmaceutically acceptable salt thereof, is less than its therapeutically effective amount would be where the second therapeutic agent is not administered. In another embodiment, the therapeutically effective amount of the second therapeutic agent is less than its therapeutically effective amount would be where Compound (I), or a pharmaceutically acceptable salt thereof, is not administered. In this way, undesired side effects associated with high doses of either agent may be minimized. Other potential advantages (including without limitation improved dosing regimens and/or reduced drug cost) will be apparent to those of skill in the art.

In yet another aspect, the invention provides the use of Compound (I), or a pharmaceutically acceptable salt thereof (i.e., an equivalent amount of a pharmaceutically acceptable salt, such as the phosphate salt), alone or together with one or more of the above-described second therapeutic agents in the manufacture of a medicament, either as a single composition or as separate dosage forms, for treatment or prevention in a subject of a disease, disorder or symptom set forth above. Another aspect of the invention is Compound (I), or a pharmaceutically acceptable salt thereof, for use in the treatment or prevention in a subject of a disease, disorder or symptom thereof delineated herein.

Pharmaceutical Compositions

A pharmaceutical composition comprising Compound (I), in the range of about 4 mg to about 50 mg (for example, about 5 mg, about 10 mg, about 20 mg, about 30 mg, about 40 mg, or about 50 mg), or an equivalent amount of a pharmaceutically acceptable salt thereof, together with a pharmaceutically acceptable carrier or diluent can be used in the method of treating hair loss described herein. In certain embodiments, the amount of Compound (I), or a pharmaceutically acceptable salt thereof, is about 4 mg, 8 mg, 16 mg, 24 mg, 32 mg or 48 mg. In certain embodiments, the amount of Compound (I), or a pharmaceutically acceptable salt thereof, is 4 mg, 8 mg, 12 mg, or 16 mg. In certain embodiments, the amount of Compound (I), or a pharmaceutically acceptable salt thereof, is 5.3 mg of Compound (I) phosphate. In certain embodiments, the amount of Compound (I), or a pharmaceutically acceptable salt thereof, is 10.5 or 10.6 mg of Compound (I) phosphate. In certain embodiments, the amount of Compound (I), or a pharmaceutically acceptable salt thereof, is 15.8 mg of Compound (I) phosphate. In certain embodiments, the amount of Compound (I), or a pharmaceutically acceptable salt thereof, is 21.1 mg of Compound (I) phosphate. In certain embodiments, the pharmaceutical composition is a tablet.

Another aspect of the invention is the use of a unit dose form comprising Compound (I), in the range of about 4 mg to about 50 mg (for example, about 5 mg, about 10 mg, about 20 mg, about 30 mg, about 40 mg, or about 50 mg), or an equivalent amount of a pharmaceutically acceptable salt thereof, together with a pharmaceutically acceptable carrier or diluent in the method of treating hair loss described herein. In certain embodiments, the amount of Compound (I), or a pharmaceutically acceptable salt thereof, is about 4 mg, 8 mg, 16 mg, 24 mg, 32 mg or 48 mg. In certain embodiments, the amount of Compound (I), or a pharmaceutically acceptable salt thereof, is 4 mg, 8 mg, 12 mg, or 16 mg. In certain embodiments, the amount of Compound (I), or a pharmaceutically acceptable salt thereof, is 5.3 mg of Compound (I) phosphate. In certain embodiments, the amount of Compound (I), or a pharmaceutically acceptable salt thereof, is 10.5 or 10.6 mg of Compound (I) phosphate. In certain embodiments, the amount of Compound (I), or a pharmaceutically acceptable salt thereof, is 15.8 mg of Compound (I) phosphate. In certain embodiments, the amount of Compound (I), or a pharmaceutically acceptable salt thereof, is 21.1 mg of Compound (I) phosphate. In certain embodiments, the unit dose form is a tablet.

The pharmaceutical compositions comprising a therapeutically effective amount of Compound (I), or a pharmaceutically acceptable salt thereof (i.e., an equivalent amount of a pharmaceutically acceptable salt, such as the phosphate salt); and a pharmaceutically acceptable carrier can be used in the method of treating hair loss described herein. The carrier(s) are "acceptable" in the sense of being compatible with the other ingredients of the formulation and, in the case of a pharmaceutically acceptable carrier, not deleterious to the recipient thereof in an amount used in the medicament. In certain embodiments, the pharmaceutical composition is provided as a unit dose form.

The invention provides a pharmaceutical composition comprising a pharmaceutically acceptable carrier or diluent and 4 to 50 mg of a compound represented by the following structural formula:

Compound (I)

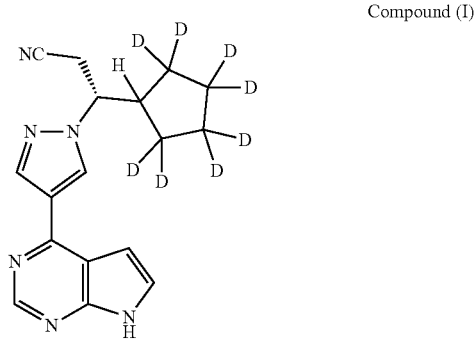

or a pharmaceutically acceptable salt thereof (i.e., an equivalent amount of a pharmaceutically acceptable salt, such as the phosphate salt) for use in the method described herein.

Pharmaceutically acceptable carriers, adjuvants and vehicles that may be used in the pharmaceutical compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

If required, the solubility and bioavailability of the compounds of the present invention in pharmaceutical compositions may be enhanced by methods well-known in the art. One method includes the use of lipid excipients in the formulation. See "Oral Lipid-Based Formulations: Enhancing the Bioavailability of Poorly Water-Soluble Drugs (Drugs and the Pharmaceutical Sciences)," David J. Hauss, ed. Informa Healthcare, 2007; and "Role of Lipid Excipients in Modifying Oral and Parenteral Drug Delivery: Basic Principles and Biological Examples," Kishor M. Wasan, ed. Wiley-Interscience, 2006.

Another known method of enhancing bioavailability is the use of an amorphous form of a compound of this invention optionally formulated with a poloxamer, such as LUTROL™ and PLURONIC™ (BASF Corporation), or block copolymers of ethylene oxide and propylene oxide. See U.S. Pat. No. 7,014,866; and United States patent publications 20060094744 and 20060079502.

The pharmaceutical compositions of the invention include those suitable for oral administration. Other formulations may conveniently be presented in unit dosage form, e.g., tablets, sustained release capsules, granules, and in liposomes, and may be prepared by any methods well known in the art of pharmacy. See, for example, Remington: The Science and Practice of Pharmacy, Lippincott Williams & Wilkins, Baltimore, MD (20th ed. 2000).

Such preparative methods include the step of bringing into association with the molecule to be administered ingredients such as the carrier that constitutes one or more accessory ingredients. In general, the compositions are prepared by uniformly and intimately bringing into association the active ingredients with liquid carriers, liposomes or finely divided solid carriers, or both, and then, if necessary, shaping the product.

In certain embodiments, the compound is administered orally. Compositions of the present invention suitable for oral administration may be presented as discrete units such as capsules, sachets, or tablets each containing a predetermined amount of the active ingredient; a powder or granules; a solution or a suspension in an aqueous liquid or a non-aqueous liquid; an oil-in-water liquid emulsion; a water-in-oil liquid emulsion; packed in liposomes; or as a bolus, etc. Soft gelatin capsules can be useful for containing such suspensions, which may beneficially increase the rate of compound absorption. In a specific embodiment, the compound is administered orally as a tablet.

In the case of tablets for oral use, carriers that are commonly used include lactose and corn starch. Lubricating agents, such as magnesium stearate, are also typically added. For oral administration in a capsule form, useful diluents include lactose and dried cornstarch. When aqueous suspensions are administered orally, the active ingredient is combined with emulsifying and suspending agents. If desired, certain sweetening and/or flavoring and/or coloring agents may be added. In another embodiment, the composition is in the form of a tablet. In certain embodiments, exemplary formulations for the tablet are disclosed in U.S. Pat. No. 8,754,224, the teachings of which are herein incorporated by reference.

In a particular embodiment, a tablet formulation contains about 4 mg to about 50 mg of Compound (I), or an equivalent amount of a pharmaceutically acceptable salt thereof (such as the phosphate salt), and the following inactive ingredients: colloidal silicon dioxide, magnesium stearate, microcrystalline cellulose, and povidone. Wet granulation followed by compression provides tablets comprising Compound (I), or a pharmaceutically acceptable salt thereof. For example, to prepare a 200 mg tablet comprising the equivalent of 16 mg of Compound (I), 10.6 wt % of Compound (I) phosphate and 64.44 wt % Avicel PH-101 microcrystalline cellulose are mixed in a higher shear granulator, and an 8.5% w/w aqueous Kollidon 30 solution (containing Kollidon 30, a polyvinylpyrrolidone (povidone); 5 wt % (based on the total formulation weight) is added during mixing to form granules. The granules are tray-dried in an oven at 60±10° C. and milled using a Quadro Comil U5 mill. The granules retained on the comil screen are forced through a #20 mesh sieve using a stainless steel spatula. The resulting milled granules are mixed with Avicel PH-200 microcrystalline cellulose (18.5 wt %), Aerosil 200 colloidal silicon dioxide (0.5 wt %) and Hyqual magnesium stearate (1 wt %) in a Turbula mixer to form the final blend. The final blend is compressed into 200 mg tablets using a Riva Piccola rotary press tooled with 0.451"×0.229" D-type modified capsule shape tooling. Each tablet contains 21.1 mg Compound (I) (equivalent to 16 mg of Compound (I) free base).

In a particular embodiment, the tablet contains about 10.5 mg or about 10.6 mg of the phosphate salt of Compound (I) (equivalent to 8 mg of Compound (I) free base).

In a particular embodiment, the tablet comprises the following ingredients:

| 4 mg Tablet | | | |
|---|---|---|---|
| Component | Function | Wt % | Amount per unit (mg) |
| Compound (I) Phosphate | Active | 2.6 | 5.3* |
| Microcrystalline Cellulose | Diluent/Binder | 90.9 | 181.7 |
| Povidone | Binder | 5.0 | 10.0 |
| Colloidal Silicon Dioxide | Glidant | 0.5 | 1.0 |
| Magnesium Stearate | Lubricant | 1.0 | 2.0 |
| Purified Water | Solvent | Removed during processing | |
| Total | | 100.0 | 200.0 |

*Equivalent to 4 mg Compound (I) free base

In another particular embodiment, the tablet comprises the following ingredients:

| 8 mg Tablet | | | |
|---|---|---|---|
| Component | Function | Wt % | Amount per unit (mg) |
| Compound (I) Phosphate | Active | 5.2 | 10.5* |
| Microcrystalline Cellulose | Diluent/Binder | 90.8 | 181.5 |
| Povidone | Binder | 2.5 | 5.0 |
| Colloidal Silicon Dioxide | Glidant | 0.5 | 1.0 |
| Magnesium Stearate | Lubricant | 1.0 | 2.0 |
| Purified Water | Solvent | Removed during processing | |
| Total | | 100.0 | 200.0 |

*Equivalent to 8 mg Compound (I) free base

In an alternative particular embodiment, the tablet comprises the following ingredients:

| 8 mg Tablet | | | |
|---|---|---|---|
| Component | Function | Wt % | Amount per unit (mg) |
| Compound (I) Phosphate | Active | 5.3 | 10.6* |
| Microcrystalline Cellulose | Diluent/Binder | 88.2 | 176.4 |
| Povidone | Binder | 5.0 | 10.0 |
| Colloidal Silicon Dioxide | Glidant | 0.5 | 1.0 |
| Magnesium Stearate | Lubricant | 1.0 | 2.0 |
| Purified Water | Solvent | Removed during processing | |
| Total | | 100.0 | 200.0 |

*Equivalent to 8 mg Compound (I) free base

In still another particular embodiment, the tablet comprises the following ingredients:

| 16 mg Tablet | | | |
|---|---|---|---|
| Component | Function | Wt % | Amount per unit (mg) |
| Compound (I) Phosphate | Active | 10.6 | 21.1* |
| Microcrystalline Cellulose | Diluent/Binder | 82.9 | 165.9 |
| Povidone | Binder | 5.0 | 10.0 |
| Colloidal Silicon Dioxide | Glidant | 0.5 | 1.0 |
| Magnesium Stearate | Lubricant | 1.0 | 2.0 |
| Purified Water | Solvent | Removed during processing | |
| Total | | 100.0 | 200.0 |

*Equivalent to 16 mg Compound (I) free base

In another embodiment, a composition of this invention further comprises a second therapeutic agent. The second therapeutic agent may be selected from any compound or therapeutic agent known to have or that demonstrates advantageous properties when administered with a compound having the same mechanism of action as ruxolitinib.

Preferably, the second therapeutic agent is an agent useful in the treatment of hair loss disorders or autoimmune conditions, including inhibitors of JAK1, JAK2, or JAK3, and/or STAT1. Such inhibitors include ruxolitinib, tofacitinib, baricitinib, filgotinib, and the like. Other second therapeutic agents include oral corticosteroids.

In another embodiment, the invention provides separate dosage forms of Compound (I), or a pharmaceutically acceptable salt thereof, and one or more of any of the above-described second therapeutic agents, wherein Compound (I), or a pharmaceutically acceptable salt thereof, and second therapeutic agent are associated with one another. The term "associated with one another" as used herein means that the separate dosage forms are packaged together or otherwise attached to one another such that it is readily apparent that the separate dosage forms are intended to be sold and administered together (within less than 24 hours of one another, consecutively or simultaneously).

In the pharmaceutical compositions of the invention, Compound (I), or a pharmaceutically acceptable salt thereof, is present in a therapeutically effective amount. As used herein, the term "therapeutically effective amount" refers to an amount which, when administered in a proper dosing regimen, is sufficient to treat the target disorder.

The interrelationship of dosages for animals and humans (based on milligrams per meter squared of body surface) is described in Freireich et al., Cancer Chemother. Rep, 1966, 50: 219. Body surface area may be approximately determined from height and weight of the subject. See, e.g., Scientific Tables, Geigy Pharmaceuticals, Ardsley, N.Y., 1970, 537.

In one embodiment, a therapeutically effective amount of Compound (I) (either as the free base, or as an equivalent amount of a pharmaceutically acceptable salt, such as the phosphate salt) can range from about 4 mg to 50 mg per day (such as 4 mg to 50 mg per day), such as, about 5 mg/day (such as 5 mg/day), about 10 mg/day (such as 10 mg/day), about 20 mg/day (such as 20 mg/day), about 30 mg/day (such as 30 mg/day), about 40 mg/day (such as 40 mg/day), or about 50 mg/day (such as 50 mg/day). In certain embodiments, the amount is about 4 mg/day (such as 4 mg/day), about 8 mg/day (such as 8 mg/day), about 16 mg/day (such as 16 mg/day), about 24 mg/day (such as 24 mg/day), about 32 mg/day (such as 32 mg/day) or about 48 mg/day (such as 48 mg/day). In one embodiment, a dose of about 4 mg/day (such as 4 mg/day), about 8 mg/day (such as 8 mg/day), about 16 mg/day (such as 16 mg/day), about 24 mg/day (such as 24 mg/day), about 32 mg/day (such as 32 mg/day) or about 48 mg/day (such as 48 mg/day) is administered once a day. In a specific example, a dose of 16 mg/day is administered as two 8 mg tablets of Compound (I) (either as the free base, or as an equivalent amount of a pharmaceutically acceptable salt, such as the phosphate salt) administered together (i.e., as a single dose). In another specific example, a dose of 16 mg/day is administered as one 16 mg tablet of Compound (I) (either as the free base, or as an equivalent amount of a pharmaceutically acceptable salt, such as the phosphate salt). In another embodiment, a dose of 4 mg/day, 8 mg/day, 16 mg/day, 24 mg/day, 32 mg/day or 48 mg/day is administered in divided doses, twice a day (e.g., a 48 mg/day dose is administered as 24 mg twice daily). In another embodiment, a dose of 8 mg/day, 16 mg/day, 24 mg/day, or 32 mg/day is administered in divided doses, twice a day (e.g., a 32 mg/day dose is administered as 16 mg of Compound (I) (either as the free base, or as an equivalent amount of a pharmaceutically acceptable salt, such as the phosphate salt) twice daily, i.e., in separate doses. In one specific embodiment, a dose of 16 mg/day is administered as 8 mg of Compound (I) (either as the free base, or as an equivalent amount of a pharmaceutically acceptable salt, such as the phosphate salt) twice daily, i.e., in separate doses. It will be understood that reference to an amount of Compound (I), or a pharmaceutically acceptable salt thereof, includes an amount of a pharmaceutically acceptable salt of Compound (I) (such as the phosphate salt) which is equivalent to the stated amount of Compound (I) as the free base (e.g., 10.5 mg of Compound (I) phosphate salt is equivalent to 8 mg of Compound (I) free base).

In certain embodiments, a therapeutically effective amount of Compound (I), or a pharmaceutically acceptable salt thereof is about 4 mg (such as 4 mg) twice per day. In a specific embodiment, a therapeutically effective amount of Compound (I) is administered as about 5.3 mg (such as 5.3 mg) of the phosphate salt of Compound (I) twice per day. In certain embodiments, a therapeutically effective amount of Compound (I), or a pharmaceutically acceptable salt thereof is about 8 mg (such as 8 mg) twice per day. In a specific embodiment, Compound (I) is administered as about 10.5 mg (such as 10.5 mg) of the phosphate salt of Compound (I) twice per day.

In certain embodiments, a therapeutically effective amount of Compound (I), or a pharmaceutically acceptable salt thereof is about 12 mg (such as 12 mg) twice per day. In a specific embodiment, a therapeutically effective amount of Compound (I) is about 15.8 mg (such as 15.8 mg) of the phosphate salt of Compound (I) twice per day. In certain embodiments, a therapeutically effective amount of Compound (I), or a pharmaceutically acceptable salt thereof is about 16 mg (such as 16 mg) twice per day. In a specific embodiment, the therapeutically effective amount of Compound (I) is about 21.1 mg (such as 21.1 mg) of the phosphate salt of Compound (I) twice per day.

EXAMPLES

Example 1: Drug-Drug Interaction Study of CTP-543 (Compound (I)) and Itraconazole (a Strong CYP3A4 Inhibitor)

A drug-drug interaction study was conducted, wherein healthy volunteers were administered 12 mg of Compound (I) (as about 15.8 mg of the phosphate salt) on Day 1, 200 mg of itraconazole on Days 4-6, 12 mg of Compound (I) (as about 15.8 mg of the phosphate salt) and 200 mg of itraconazole on Day 7, and 200 mg of itraconazole on Day 8.

The statistical comparison of the plasma concentration data is shown in the table below:

| Parameter | 12 mg Compound (I) (Reference) | 12 mg Compound (I) with Itraconazole (Test) | Ratio (T/R) |
|---|---|---|---|
| $AUC_{(0-Tlast)}$ (ng*hr/mL) | 1326.80 | 1679.53 | 1.27 |
| $AUC_{(0-\infty)}$ (ng*hr/mL) | 1332.48 | 1686.55 | 1.27 |
| $C_{max}$ (ng/ml) | 266.26 | 300.77 | 1.13 |
| $t_{1/2}$ (hr) | 4.13 | 4.62 | |

The pharmacokinetic data show: (1) an increase in the $C_{max}$ of Compound (I) by about only 13% as a result of dosing Compound (I) with itraconazole; (2) an increase in the AUC of Compound (I) by about only 27% as a result of dosing Compound (I) with itraconazole; and (3) a change in the half-life of Compound (I) from 4.18 hours to 4.62 hours as a result of dosing Compound (I) with itraconazole. These changes seen in the pharmacokinetic parameters of Compound (I) in the presence of itraconazole (a strong CYP3A4 inhibitor) are unexpectedly much less than those reported for ruxolitinib in the presence of another strong CYP3A4 inhibitor, ketoconazole. Specifically, the prescribing label for ruxolitinib reports that the $C_{max}$ of ruxolitinib increased by 33%, the AUC increased by 91%, and the half-life increased from 3.7 hour to 6.0 hours as a result of dosing ruxolitinib with ketoconazole.

While the study described above used the CYP3A4 inhibitor itraconazole and the study reported on the prescribing label for ruxolitinib used the CYP3A4 inhibitor ketoconazole, itraconazole is reported to have a significantly lower inhibitory constant (Ki) than ketoconazole, suggesting that itraconazole is at least as strong a CYP3A4 inhibitor as ketoconazole. In addition, both ketoconazole and itraconazole are drugs that the FDA has categorized as strong CYP3A4 inhibitors that may be used in drug-drug interaction studies as index drugs. Regarding the dosing, both inhibitors were dosed at their standard doses, in accordance with the FDA Guidance.

Because the changes in the CTP543 pharmacokinetic parameters in the presence of a strong CYP3A4 inhibitor are relatively modest, and similar in magnitude to the changes in pharmacokinetic parameters reported for ruxolitinib in the presence of moderate CYP3A4 inhibitors where no dose modification is required, it would not be expected that the FDA would require a warning regarding concomitant administration of Compound (I) with strong CYP3A4 inhibitors.

This represents an unexpected benefit of Compound (I) over ruxolitinib, particularly for a certain subset of patients taking a CYP3A4 inhibitor, given that the ruxolitinib prescribing information carries a warning regarding concomitant dosing with strong CYP3A4 inhibitors. Patients often are prescribed strong CYP3A4 inhibitors, such as those listed in the ruxolitinib prescribing information or in the FDA table of inhibitors for drug-drug interactions. A drug that does not require dose adjustment or interruption when co-administered with strong CYP3A4 inhibitors is a clinical advantage.

Without further description, it is believed that one of ordinary skill in the art can, using the preceding description and the illustrative examples, make and utilize the compounds of the present invention and practice the claimed methods. It should be understood that the foregoing discussion and examples merely present a detailed description of certain preferred embodiments. It will be apparent to those of ordinary skill in the art that various modifications and equivalents can be made without departing from the spirit and scope of the invention.

What is claimed is:

1. A method of treating a hair loss disorder in a human subject in need thereof, the method comprising orally administering to the human subject about 4 mg to about 50 mg of Compound (I) represented by the following structural formula:

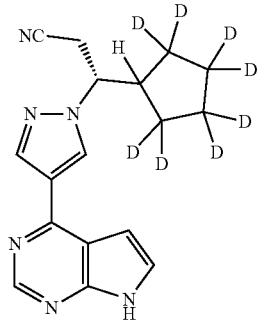

Compound (I)

or a pharmaceutically acceptable salt thereof, wherein each position designated specifically as deuterium has at least 95% incorporation of deuterium; and wherein:
  (i) about 0.1 mg to about 200 mg of a CYP3A4 inhibitor is being co-administered to the human subject; and
  (ii) no adjustment of the dosage of Compound (I), or a pharmaceutically acceptable salt thereof, is required due to the co-administering of the CYP3A4 inhibitor, wherein the hair loss disorder is alopecia areata, alopecia totalis or alopecia universalis.

2. The method of claim 1, wherein the hair loss disorder is alopecia areata.

3. The method of claim 1, wherein Compound (I), or a pharmaceutically acceptable salt thereof, is administered at about 16 mg/day, or about 24 mg/day, wherein the about 16 mg/day of Compound (I) or pharmaceutically acceptable salt thereof is administered as about 8 mg twice per day and the about 24 mg/day of the compound or pharmaceutically acceptable salt thereof is administered as about 12 mg twice per day.

4. The method of claim 1, wherein Compound (I), or a pharmaceutically acceptable salt thereof, is administered in a pharmaceutical formulation which is a tablet.

5. The method of claim 1, wherein the human subject's SALT score is less than or equal to 20 after treatment.

6. The method of claim 1, wherein the CYP3A4 inhibitor is a strong CYP3A4 inhibitor.

7. The method of claim 1, wherein no interruption of the administration of the CYP3A4 inhibitor is required.

8. A method of treating a hair loss disorder in a human subject in need thereof, the method comprising orally administering to the human subject about 4 mg to about 50 mg of Compound (I) represented by the following structural formula:

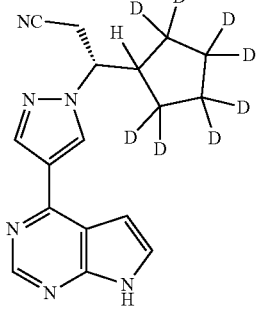

Compound (I)

or a pharmaceutically acceptable salt thereof, wherein each position designated specifically as deuterium has at least 95% incorporation of deuterium; and wherein:
  (ii) the subject is receiving a concomitant administration of about 0.1 mg to about 200 mg of a CYP3A4 inhibitor; and
  (ii) the amount of Compound (I), or a pharmaceutically acceptable salt thereof, is not reduced compared to the amount of Compound (I), or pharmaceutically acceptable salt thereof, that would be administered to the subject in the absence of concomitant administration of a CYP3A4 inhibitor, wherein the hair loss disorder is alopecia areata, alopecia totalis or alopecia universalis.

9. The method of claim 8, wherein the hair loss disorder is alopecia areata.

10. The method of claim 8, wherein Compound (I), or a pharmaceutically acceptable salt thereof, is administered at about 16 mg/day, or about 24 mg/day, wherein the about 16 mg/day of Compound (I) or pharmaceutically acceptable salt thereof is administered as about 8 mg twice per day and the about 24 mg/day of the compound or pharmaceutically acceptable salt thereof is administered as about 12 mg twice per day.

11. The method of claim 8, wherein Compound (I), or a pharmaceutically acceptable salt thereof, is administered in a pharmaceutical formulation which is a tablet.

12. The method of claim 8, wherein the human subject's SALT score is less than or equal to 20 after treatment.

13. The method of claim 8, wherein the CYP3A4 inhibitor is a strong CYP3A4 inhibitor.

14. The method of claim 8, wherein no interruption of the administration of the CYP3A4 inhibitor is required.

15. A method of treating a hair loss disorder in a human subject in need thereof, the method comprising orally administering to the human subject about 4 mg to about 50 mg of Compound (I) represented by the following structural formula:

Compound (I)

or a pharmaceutically acceptable salt thereof, wherein each position designated specifically as deuterium has at least 95% incorporation of deuterium; and wherein:
  (i) the subject has been determined to be receiving a concomitant administration of about 0.1 mg to about 200 mg of a CYP3A4 inhibitor; and
  (ii) the amount of Compound (I), or a pharmaceutically acceptable salt thereof, is not reduced compared to the amount of Compound (I), or pharmaceutically acceptable salt thereof, that would be administered to the subject in the absence of concomitant administration of a CYP3A4 inhibitor, wherein the hair loss disorder is alopecia areata, alopecia totalis or alopecia universalis.

16. The method of claim 15, wherein the hair loss disorder is alopecia areata.

17. The method of claim 15, wherein Compound (I), or a pharmaceutically acceptable salt thereof, is administered at about 16 mg/day, or about 24 mg/day, wherein the about 16 mg/day of Compound (I) or pharmaceutically acceptable salt thereof is administered as about 8 mg twice per day and the about 24 mg/day of the compound or pharmaceutically acceptable salt thereof is administered as about 12 mg twice per day.

18. The method of claim 15, wherein Compound (I), or a pharmaceutically acceptable salt thereof, is administered in a pharmaceutical formulation which is a tablet.

19. The method of claim 15, wherein the human subject's SALT score is less than or equal to 20 after treatment.

20. The method of claim 15, wherein the CYP3A4 inhibitor is a strong CYP3A4 inhibitor.

21. The method of claim 15, wherein no interruption of the administration of the CYP3A4 inhibitor is required.

22. A method of treating a hair loss disorder in a human subject in need thereof, the method comprising:
  (iii) determining if the human subject is receiving a concomitant administration of a CYP3A4 inhibitor; and
  (iv) orally administering to the human subject about 4 mg to about 50 mg of Compound (I) if the subject is receiving concomitant administration of about 0.1 mg to about 200 mg of a CYP3A4 inhibitor, wherein Compound (I) is represented by the following structural formula:

Compound (I)

or a pharmaceutically acceptable salt thereof, wherein each position designated specifically as deuterium has at least 95% incorporation of deuterium; and
wherein, the amount of Compound (I), or a pharmaceutically acceptable salt thereof, is not reduced compared to the amount of Compound (I), or pharmaceutically acceptable salt thereof, that would be administered to the subject in the absence of concomitant administration of a CYP3A4 inhibitor, wherein the hair loss disorder is alopecia areata, alopecia totalis or alopecia universalis.

23. The method of claim 22, wherein the hair loss disorder is alopecia areata.

24. The method of claim 22, wherein Compound (I), or a pharmaceutically acceptable salt thereof, is administered at about 16 mg/day, or about 24 mg/day, wherein the about 16 mg/day of Compound (I) or pharmaceutically acceptable salt thereof is administered as about 8 mg twice per day and the about 24 mg/day of the compound or pharmaceutically acceptable salt thereof is administered as about 12 mg twice per day.

25. The method of claim 22, wherein Compound (I), or a pharmaceutically acceptable salt thereof, is administered in a pharmaceutical formulation which is a tablet.

26. The method of claim 22, wherein the human subject's SALT score is less than or equal to 20 after treatment.

27. The method of claim 22, wherein the CYP3A4 inhibitor is a strong CYP3A4 inhibitor.

28. The method of claim 22, wherein no interruption of the administration of the CYP3A4 inhibitor is required.

* * * * *